United States Patent
Hancock

(10) Patent No.: US 8,758,385 B2
(45) Date of Patent: Jun. 24, 2014

(54) HIGH SPECIFIC GRAVITY INTRAGASTRIC DEVICE

(76) Inventor: John Hancock, Santa Barbara, CA (US)

( * ) Notice: Subject to any disclaimer, the term of this patent is extended or adjusted under 35 U.S.C. 154(b) by 656 days.

(21) Appl. No.: 12/645,466

(22) Filed: Dec. 22, 2009

(65) Prior Publication Data

US 2010/0168782 A1    Jul. 1, 2010

Related U.S. Application Data

(60) Provisional application No. 61/140,952, filed on Dec. 27, 2008.

(51) Int. Cl.
*A61M 29/00*    (2006.01)

(52) U.S. Cl.
USPC .......................................... 606/192

(58) Field of Classification Search
CPC ................... A61B 17/12022; A61B 17/12036; A61B 17/1204; A61B 17/12136; A61M 29/00; A61F 5/0003
USPC .......................... 606/191, 192, 195, 198, 108; 604/96.01–103.14, 270, 509; 623/23.64, 23.65, 23.67; 600/37
See application file for complete search history.

(56) References Cited

U.S. PATENT DOCUMENTS

| 4,416,267 A | 11/1983 | Garren et al. |
|---|---|---|
| 4,485,805 A | 12/1984 | Foster, Jr. |
| 4,607,618 A | 8/1986 | Angelchik |
| 4,675,174 A | 6/1987 | Eckenhoff |
| 4,739,758 A | 4/1988 | Lai et al. |
| 4,899,747 A | 2/1990 | Garren et al. |
| 4,992,312 A | 2/1991 | Frisch |
| 5,084,061 A | 1/1992 | Gau et al. |
| 5,176,636 A | 1/1993 | Wild |
| 5,234,454 A | 8/1993 | Bangs |

(Continued)

FOREIGN PATENT DOCUMENTS

| CN | 1575155 | 2/2005 |
|---|---|---|
| WO | WO 2007/142503 | 12/2007 |

(Continued)

OTHER PUBLICATIONS

International Search Report for PCT/US2009/069351, Aug. 13, 2010, Hancock.

(Continued)

*Primary Examiner* — Katherine Dowe
(74) *Attorney, Agent, or Firm* — Brian S. Boyer; Syndicated Law, PC

(57) ABSTRACT

The teachings are directed to an intragastric device comprising a flexible and expandable bladder having a predetermined shape upon expansion for contacting the antrum of the stomach of a subject. The device is designed to avoid passage of any part of the device beyond the pylorus and lower esophageal sphincter while the bladder is expanded during use. In these embodiments, the bladder can contain a high specific gravity material when expanded; wherein, the high specific gravity material contributes to an in vivo specific gravity of the device that ranges from about 1.2 g/ml to about 2.1 g/ml and functions to direct the device to the pyloric antrum of the subject during use of the device. Moreover, these embodiments can include a filling material comprising a biocompatible fluid component and a hydrogel component to make the device substantially leakproof and contribute to the in vivo specific gravity of the device.

71 Claims, 4 Drawing Sheets

(56) References Cited

U.S. PATENT DOCUMENTS

| | | | |
|---|---|---|---|
| 5,308,326 A | 5/1994 | Zimmon | |
| 5,400,770 A | 3/1995 | Nakao et al. | |
| 5,425,382 A | 6/1995 | Golden et al. | |
| 5,433,216 A * | 7/1995 | Sugrue et al. | 600/591 |
| 5,578,005 A | 11/1996 | Sancoff et al. | |
| 5,622,169 A | 4/1997 | Golden et al. | |
| 5,653,240 A | 8/1997 | Zimmon | |
| 5,707,355 A | 1/1998 | Zimmon | |
| 5,709,657 A | 1/1998 | Zimmon | |
| 5,785,684 A | 7/1998 | Zimmon | |
| 5,879,297 A | 3/1999 | Haynor et al. | |
| 5,902,238 A | 5/1999 | Golden et al. | |
| 5,906,587 A | 5/1999 | Zimmon | |
| 5,947,926 A | 9/1999 | Zimmon | |
| 5,993,473 A | 11/1999 | Chan et al. | |
| 5,997,546 A | 12/1999 | Foster et al. | |
| 6,013,854 A | 1/2000 | Moriuchi | |
| 6,030,361 A | 2/2000 | Miyashiro | |
| 6,129,668 A | 10/2000 | Haynor et al. | |
| 6,203,520 B1 | 3/2001 | Zimmon | |
| 6,216,028 B1 | 4/2001 | Haynor et al. | |
| 6,263,230 B1 | 7/2001 | Haynor et al. | |
| 6,315,733 B1 | 11/2001 | Zimmon | |
| 6,419,699 B1 | 7/2002 | Schuessler | |
| 6,535,764 B2 | 3/2003 | Imran et al. | |
| 6,579,301 B1 | 6/2003 | Bales et al. | |
| 6,656,194 B1 | 12/2003 | Gannoe et al. | |
| 6,746,460 B2 | 6/2004 | Gannoe | |
| 6,773,452 B2 | 8/2004 | Shaker | |
| 6,808,521 B1 | 10/2004 | McMichael | |
| 6,923,786 B2 | 8/2005 | Rouns et al. | |
| 6,955,690 B1 | 10/2005 | Cao | |
| 6,981,980 B2 | 1/2006 | Sampson et al. | |
| 6,994,095 B2 | 2/2006 | Burnett | |
| 7,016,735 B2 | 3/2006 | Imran et al. | |
| 7,020,531 B1 | 3/2006 | Colliou et al. | |
| 7,033,373 B2 | 4/2006 | de la Torre | |
| 7,037,343 B2 | 5/2006 | Imran | |
| 7,037,344 B2 | 5/2006 | Kagan et al. | |
| 7,056,305 B2 | 6/2006 | Garza Alvarez | |
| 7,066,945 B2 | 6/2006 | Hashiba et al. | |
| 7,076,305 B2 | 7/2006 | Imran et al. | |
| 7,107,100 B2 | 9/2006 | Imran et al. | |
| 7,120,498 B2 | 10/2006 | Imran et al. | |
| 7,167,750 B2 | 1/2007 | Knudson et al. | |
| 7,184,812 B2 | 2/2007 | Sinderby et al. | |
| 7,220,284 B2 | 5/2007 | Kagan et al. | |
| 7,291,160 B2 | 11/2007 | DeLegge | |
| 7,309,341 B2 | 12/2007 | Ortiz et al. | |
| 7,320,696 B2 | 1/2008 | Gazi et al. | |
| 7,354,454 B2 | 4/2008 | Stack et al. | |
| 7,371,215 B2 | 5/2008 | Colliou et al. | |
| 7,430,450 B2 | 9/2008 | Imran | |
| 7,431,725 B2 | 10/2008 | Stack et al. | |
| 7,444,183 B2 | 10/2008 | Knudson et al. | |
| 7,452,363 B2 | 11/2008 | Ortiz | |
| 7,483,754 B2 | 1/2009 | Imran et al. | |
| 7,490,602 B2 | 2/2009 | Sabri | |
| 7,502,649 B2 | 3/2009 | Ben-Haim et al. | |
| 2004/0186502 A1 | 9/2004 | Sampson | |
| 2004/0186503 A1 | 9/2004 | Delagge | |
| 2004/0267378 A1 | 12/2004 | Gazi | |
| 2005/0033331 A1* | 2/2005 | Burnett et al. | 606/154 |
| 2005/0159769 A1 | 7/2005 | Alverdy | |
| 2005/0267595 A1 | 12/2005 | Chen et al. | |
| 2005/0267596 A1* | 12/2005 | Chen et al. | 623/23.67 |
| 2006/0155259 A1 | 7/2006 | MacLay | |
| 2006/0161111 A1 | 7/2006 | Potter et al. | |
| 2007/0100369 A1 | 5/2007 | Cragg et al. | |
| 2007/0110784 A1 | 5/2007 | Cheng et al. | |
| 2007/0118168 A1 | 5/2007 | Lointier et al. | |
| 2007/0135829 A1 | 6/2007 | Paganon | |
| 2007/0135831 A1 | 6/2007 | Burnett | |
| 2007/0149994 A1 | 6/2007 | Sosnowski et al. | |
| 2007/0178160 A1 | 8/2007 | Burnett | |
| 2007/0198039 A1 | 8/2007 | Jones et al. | |
| 2007/0276428 A1 | 11/2007 | Haller et al. | |
| 2007/0293885 A1 | 12/2007 | Binmoeller | |
| 2008/0051823 A1 | 2/2008 | Makower et al. | |
| 2008/0097513 A1* | 4/2008 | Kaji et al. | 606/192 |
| 2008/0109027 A1 | 5/2008 | Chen et al. | |
| 2008/0161717 A1 | 7/2008 | Gertner et al. | |
| 2008/0188766 A1 | 8/2008 | Gertner et al. | |
| 2008/0208239 A1 | 8/2008 | Annunziata | |
| 2008/0208240 A1 | 8/2008 | Paz | |
| 2008/0208241 A1 | 8/2008 | Weiner et al. | |
| 2008/0215076 A1 | 9/2008 | Baker | |
| 2008/0221595 A1 | 9/2008 | Surti | |
| 2008/0221702 A1 | 9/2008 | Wallace et al. | |
| 2008/0234718 A1 | 9/2008 | Paganon et al. | |
| 2008/0241094 A1 | 10/2008 | Burnett et al. | |
| 2008/0243071 A1 | 10/2008 | Quijano et al. | |
| 2008/0249635 A1 | 10/2008 | Weitzner et al. | |
| 2008/0262529 A1 | 10/2008 | Jacques | |
| 2008/0281257 A1 | 11/2008 | Waller | |
| 2008/0306506 A1 | 12/2008 | Leatherman | |
| 2008/0312678 A1 | 12/2008 | Pasricha | |
| 2008/0319471 A1 | 12/2008 | Sosnowski et al. | |
| 2009/0012553 A1 | 1/2009 | Swain et al. | |
| 2009/0048624 A1 | 2/2009 | Alverdy | |
| 2009/0082644 A1* | 3/2009 | Li | 600/302 |
| 2009/0118756 A1 | 5/2009 | Valencon et al. | |
| 2009/0118757 A1 | 5/2009 | Burnett et al. | |
| 2009/0118758 A1 | 5/2009 | Burnett et al. | |
| 2009/0171383 A1 | 7/2009 | Cole et al. | |
| 2009/0182357 A1 | 7/2009 | Burnett et al. | |
| 2009/0182358 A1 | 7/2009 | Burnett et al. | |
| 2009/0182424 A1 | 7/2009 | Marco et al. | |
| 2009/0187200 A1 | 7/2009 | Burnett et al. | |
| 2009/0187201 A1 | 7/2009 | Burnett et al. | |
| 2009/0198210 A1 | 8/2009 | Burnett et al. | |
| 2009/0216262 A1 | 8/2009 | Burnett et al. | |
| 2009/0259236 A2 | 10/2009 | Burnett et al. | |
| 2009/0287231 A1 | 11/2009 | Brooks et al. | |
| 2009/0299486 A1 | 12/2009 | Shohat et al. | |

FOREIGN PATENT DOCUMENTS

| | | |
|---|---|---|
| WO | WO 2008/101307 | 8/2008 |
| WO | WO 2008/106041 | 9/2008 |
| WO | WO 2009/033049 | 3/2009 |
| WO | PCT/US2009/069351 | 12/2009 |

OTHER PUBLICATIONS

Mintchev, M.P., et al., Pilot Study of Temporary Controllable Gastric Pseudobezoars for Dynamic Non-Invasive Gastric Volume Reduction, Physiol Meas, Feb. 2010, 31(2), 131-144.

Sannino, A., et al., Development and Characterization of Cellulose-Based Hydrogels for Use as Dietary Bulking Agent, Journal of Applied Polymer Science, Feb. 5, 2010, 115(3), 1438-1444.

Carvalho, G.L., et al., An Improved Intragastric Balloon Procedure Using a New Balloon: Preliminary Analysis of Safety and Efficiency, *Obes Surg*, 2009, 19, 237-242.

Chan, A.O.O., et al., The effect of Intragastric Balloon Placement on Weight Loss and Type 2 Diabetes Control, *Aliment Pharmacol Ther.*, Jul. 2008, 28(1), 162-164.

Clarke, G.M. et al., Comparative gastrointestinal transit of pellet systems of varying density, *International Journal of Pharmaceutics*, Jan. 1995, 114, 1(31), 1-11.

Coskun, H., et al., BioEnterics Intragastric Balloon: Clinical Outcomes of the First 100 Patients—A Turkish Experience, Obes Surg, Sep. 2008, 18(9), 1154-1156.

Crea, N., et al., Improvement of Metabolic Syndrome Following Intragastric Balloon: 1 Year Follow-Up Analysis, Obes Surg, Aug. 2009, 19(8), 1084-1088.

Dumonceau J.M., Evidence-based review of the Bioenterics intragastric balloon for weight loss, *Obesity Surgery*, Dec. 2008, 18(12):1611-1617.

Escudero Sanchis, A., et al., Effectiveness, Safety, and Tolerability of Intragastric Balloon in Association With Low-Calorie Diet for the Treatment of Obese Patients, *Rev Esp Enferm Dig*, 2008, 100(6), 349-354.

(56) References Cited

OTHER PUBLICATIONS

Falconi, M., Stomach Balloons Used to Fight Weight Gain, [online] [retrieved Mar. 2, 2010] URL: http://www.obesitydiscussion.com/forums/obesity-surgery/stomach-balloons-used-fight-weight-588.html.

Jones, K.L., et al, Relation between postprandial satiation and antral area in normal subjects, *American Journal of Clinical Nutrition*, Jul. 1997, 66(1), 127-32.

Jones, K.L., et al., Effects of posture on gastric emptying, transpyloric flow, and hunger after a glucose drink in healthy humans, *Digestive Disease Science*, Aug. 2006, 51(8), 1331-1338.

Katoh, K. et al., Passage of indigestible particles of various specific gravities in sheep and goats, *British Journal of Nutrition*, 1988, 60, 683-687.

Kotzampassi, K., et al., Intragastric Balloon: Ethics, Medical Need and Cosmetics, *Dig Dis.*, 2008, 26(1), 45-48.

Lakdawalla, D. N., et al., The Health and Cost Consequences of Obesity Among the Future Elderly, *Health Aff*, Sep. 26, 2005, 24 Suppl 2, W5R30-41.

Lopasso, F. P. et al., A Pilot Study to Evaluate the Safety, Tolerance and Efficacy of a Novel Stationary Antral Balloon (SAB) for Obesity, *J. Clin Gastroenterol*, Jan. 1, 2008, 42(1), 48-53.

Mathus-Vliegen, EM, Intragastric Balloon Treatment for Obesity: What Does it Really Offer?, *Dig Dis.*, 2008, 26(1), 40-44.

Mundt, MW, et al., Relationships between gastric accommodation and gastrointestinal sensations in healthy volunteers. A study using the barostat technique and two- and three-dimensional ultrasonography, *Digestive Disease Science*, Sep. 2005, 50(9),1654-1660.

Senior, R, Imagify (perflubutane polymer microspheres) injectable suspension for the assessment of coronary artery disease, *Expert Review of Cardiovascular Therapy*, May 2007, 5(3), 413-21.

Vanden Berghe, P, et al., Contribution of different triggers to the gastric accommodation reflex in humans, *American Journal of Physiology. Gastroentestional and Liver Physiology*, Nov. 2009, 297(5), G902-906.

Yao, S, et al., Visceral sensitivity to gastric stimulation and its correlation with alterations in gastric emptying and accommodation in humans, *Obesity Surgery*, Feb. 2005, 15(2), 247-253.

Whalen, C.H. et al, The Bioenteric Intragastric Balloon (BIB): how to use it, *Obesity Surgery*, Aug. 2001, 11(4), 524-527.

Whitehead, L. et al., Floating dosage forms: an in vivo study demonstrating prolonged gastric retention, *Journal of Controlled Release*, Oct. 30, 1998, 55(1), 3-12.

Ziessman H.A. et al., The effect of the Garren-Edwards Gastric Bubble on solid and liquid gastric emptying, *Clinical Nuclear Medicine*, Aug. 1988, 13(8), 586-589.

Zumbuehl, A, et al., Antifungal Hydrogels, *Proceedings of the National Academy of Sciences of the United States of America*, Aug. 7, 2007, 104(32), 12994-12998.

Economic Costs of Diabetes in the U.S. in 2002, *Diabetes Care*, Mar. 2003, 26(3), 917-932.

Efficacy of Preoperative Intra Gastric Balloon in Morbidly Obese Patients Selected for Gastric By-Pass (BIGPOM), [online] [retrieved on Jun. 24, 2010] URL: http://clinicaltrials.gov/ct2/show/study/NCT00504036.

F as in Fat: How Obesity Policies are Failing in America, 2009, Trust for America's Health [online] [retrieved on Jul. 7, 2010] URL: http://healthyamericans.org/reports/obesity2009/Obesity2009Report.pdf.

Benjamin, S.B., et al., Double-blind controlled trial of the Garren-Edwards gastric bubbles: an adjunctive treatment for exogenous obesity. Gastroentereology Sep. 1995 (3):581-8 (1998).

Bonazzi, P., et al., Gastric emptying and intragastric balloon in obese patients. Eur Rev Med Pharmacol Sci. Sep.-Oct.;9 (5 Suppl 1):15-21: (2005).

Csendes, A., et al., Size, volume and weight of the stomach in patients with morbid obesity compared to controls. Obes Surg. (2005).

Delgado-Aros, S., et al., Effect of gastric volume or emptying on meal related symptoms after liquid nutrients in obesity: a pharmacologic study. Clin Gastroenterol Hepatol Oct: 3 (10):997-1006 (2005).

Durrans, D., et al., Intragastric device for weight loss.effect on energy intake in dogs. Dig Dis Sci. Jul: 36(7):893-6 (1991).

Evans, J.T., et al, Intragastric balloon therapy in the mamagement of obesity: why the bad wrap? J Parenter Enteral Nutr, Jan: 35(1):25-31(2011).

Geliebter, A., et al., Clinical trial of silicone-rubber gastric balloon to treat obesity.Int J Obes. Apr; 15(4):259-66 (1991).

Geliebter, A., et al., Gastric balloon to treat obesity: a double-blind study in nondieting subjucts. Am J Clin NutrApr: 51 (4):584-8. (1990).

Geliebter A., et al., Gastric capacity, gastric, gastric empting, and test-meal intake in normal and bulimic women. Am J Clin Nutr. Oct; 56(4):656-61(1992).

Geliebter, A., et al., Gastric distention by balloon and test-meal intake in obese and lean subjects. Am J Clin Nutr. Sep: 48(3):592-4 (1988).

Geliebter, A., et al., Reduced stomach capacity in obese subjucts after dieting. Am J Clin Nutr Feb; 63 (2):170-3 (1996).

Geliebter, A., et al., Gastric capacity in normal, obese, and bulimic women. Pyysio Behav. Nov-Dec; 74 (4-5)743-6 (2001).

Genco, A., et al, BioEntrics intragastric balloon: The Italian experience with 2,515 patients. Obes Surg. Sep; 15 (8):1161-4 (2005).

Genco, A., et al, Intragastric balloon or diet alone? A retrospective evaluation. Obes Surg. Aug. 2008; 18(8):989-92. Epub May 16, 2008.

Hogan, R.B., et al., A double-blind, randomized, sham-controlled trial of the gastric bubble for obesity. Gastrointest Endosc. Sept-Oct; 35(5):381-5 (1989).

Imaz, I., et al., Safety and effectiveness of the intragastric balloon for obesity, A meta-analysis. Obes Surg. Jul;18(7):841-6 (2008).

Kramer, F.M., et al., Limited weight losses with a gastric balloon. Arch Intern Med. Feb: 149 (2):411-3 (1989).

Mathus-Vliegen, E.M.H., et al., Intragastric balloon in the treatment of super-morbid obesity. Double-blind, sham-controlled, crossover evaluation of 5000-milliliter balloon. Gastroenterology Aug; 99 (2):362-9 (1990).

Mion, F., et al, Tolerance and efficacy of an air-filled balloon in non-morbidly obese patients: results of a prospective multicenter study. Obes Surg. Jun; 17(6): 764-9. (2007).

Mion, F., et al, Swallowable obalon gastric ballons as an aid for weight Loss: apilot feasibility study. Obes Surf. 23:730-733. (2013).

* cited by examiner

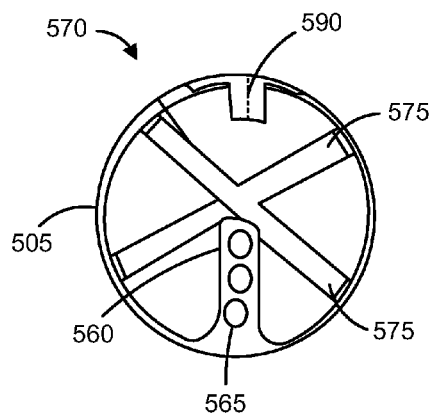 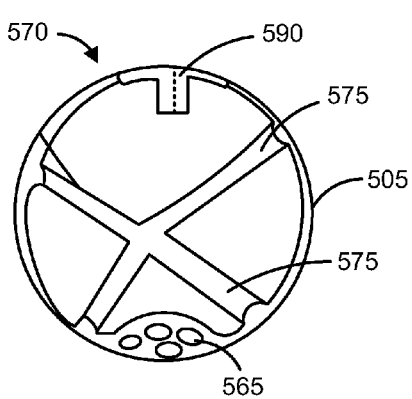
FIG. 5A  FIG. 5B
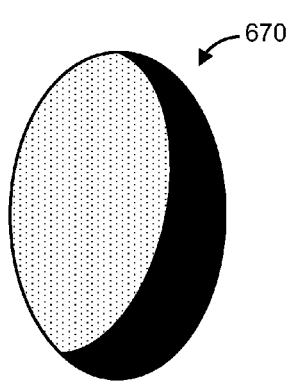 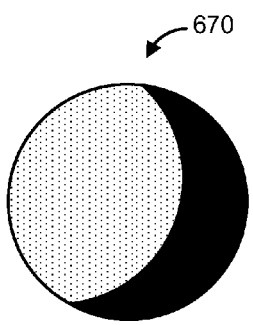 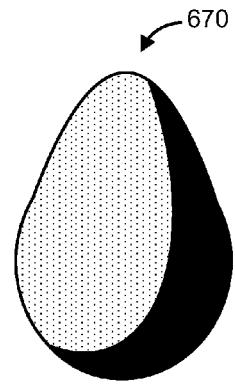
FIG. 6A  FIG. 6B  FIG. 6C

HIGH SPECIFIC GRAVITY INTRAGASTRIC DEVICE

CROSS-REFERENCE TO RELATED APPLICATIONS

This application claims the benefit of U.S. Provisional Application No. 61/140,952, filed Dec. 27, 2008, which is hereby incorporated herein by reference in its entirety.

BACKGROUND

1. Field of the Invention

The teachings provided herein are directed to a high specific gravity intragastric device, a method for delivering the device in a subject, and a method for treating obesity in the subject.

2. Description of the Related Art

Obesity is a worldwide problem that needs an effective remedy. More than one third of the adult population of the United States, for example, is considered to be obese, and, it's estimated that 27% of men and 38% of women are obese in Europe. A person can be considered "obese" if their body mass index (BMI) is greater than 30 kg/m$^2$, where the BMI can be defined as the person's weight in kg divided by the person's height in m$^2$. In fact, a person is considered "morbidly obese" if their BMI is greater than 35 kg/m$^2$. Unfortunately, approximately 23 million of the 72 million adults in the US are morbidly obese.

The problem is that obesity is linked to numerous chronic health conditions that include, for example, hypertension, hyperlipidemia, sleep apnea, type-2 diabetes, and heart disease. In addition to an obviously decreased life expectancy, obesity-associated conditions significantly increase the length of hospital stays, and make a substantial impact on overall healthcare costs, to the extent that, in late 2005, the Center for Disease Control and Prevention estimated that about 27% of all health care costs in the US are due to inactivity and excess body weight. The same year, Medicare estimated a 35% increase in costs for obese patients over the age of 70 than their non-obese counterparts. And, it's not just a cost issue for healthcare providers and insurers—it can get very personal to the obese individual. For example, there are many adverse psychosocial aspects of obesity that include alterations in feelings of well-being, a reduced quality of life, a lower income earning potential, and the social stigmatization that is commonly realized with obesity. Moreover, the decrease in lifespan associated with obesity is comparable to the effects of smoking, where a BMI greater than 25 is correlated to a reduction in lifespan by 2-4 years in persons in the age range of 30-35. A BMI above 40 has been shown to reduce lifespan by 8-10 years. Vascular disease relating to heart attacks and strokes, hypertension, and type-2 diabetes, are common causes of health conditions and mortality among the obese. Obesity is an epidemic, and society remains overwhelmed and cannot effectively deal with this serious, growing threat to the Nation's health.

Currently, a common belief is that dieting and exercise is the only true answer. Although certainly effective beyond dispute, one problem is that diet and exercise have not been the answer for most patients. Failure rates are high, and few patients actually lose enough weight to produce meaningful health benefits. One answer to the problem has been obesity surgery, acclaimed as being the most effective intervention available in the US and including, for example, restrictive, malabsorptive, and combination techniques. One problem with such surgeries is that that are currently indicated only for patients with a BMI greater than 35 kg/m$^2$. Another problem is that the costs are high, easily exceeding $20,000. As such, the public and healthcare community has been slow to adopt obesity surgery for several reasons such as, for example, a lack of insurance. Other reasons include a fear of the procedure, as well as patient and provider attitudes regarding obesity. There were 220,000 obesity surgeries in the US in 2008, and the rate of growth is over 30% per year, representing less than 2% of all obese US persons that could quality for this procedure, showing that other methods are clearly needed. Accordingly, new and effective procedures that are less costly and less invasive would be appreciated by those of skill in the art.

Currently, intragastric implant devices are used to avoid obesity surgeries. These devices are typically free floating intragastric balloons that reside in the upper stomach and have volumes ranging from about 400 cc to about 800 cc. These devices are known for creating a feeling of "fullness," increasing the time it takes to digest a meal, and having a treatment period of 6 months or less. Unfortunately, the treatment period is limited by a number of factors that include, for example, (i) expansion of the stomach around the balloon which re-establishes the normal gastric clearance and removes the feeling of fullness experienced by the patient; (ii) leakage of the balloon creating a loss of volume; and (iii) complete failure of the balloon itself. Such large devices also have some post-placement effects that can include, for example, gastric wall contractions that create repeated episodes of projectile vomiting, early explant of the device, and life-threatening gastric perforations in some cases. Another less serious problem, although embarrassing, is a noticeable bad breath, a condition induced by the growth of plaque on the larger current intragastric devices resulting in halitosis. The use of proton pump inhibitors, or PPIs, commonly prescribed for use with the current, state-of-the-art larger balloons to decrease side-effects, adds to the bad breath issue, and it also adds cost to the treatment, as well as additional risk to the patient from overmedication. Other devices have been suggested for use in the lower, more muscular portion of the stomach known as the pyloric antrum to help control appetite. The objective of placing a device in the lower stomach is to increase distention of the antral walls during meals. Inducing an antral wall distention helps induce early feelings of fullness or gastric discomfort, leading to consumption of less volume and reduced caloric intake levels. These devices have been limited to having some sort of anchoring means, such as a tail that extends past the pylorus, an anchoring flange, or some mechanism of fastening to gastrointestinal tissue.

Each of the antrum-based devices have problems that generally either relate to adverse consequences from having (a) a portion of the device that passes through the pylorus and into the duodenum; and/or, (b) a fixation means to prevent migration in the stomach. Problems from (a) can include, for example, a retraction and entanglement of a tube that extends into the duodenum, as well as providing a means for infectious materials, such as a virus or bacteria normally destroyed by stomach acids, to enter the small intestine. Problems from (b) can include blockage of the pylorus and interruption of the otherwise normal stomach functions. Other problems from both (a) and (b) can include, for example, the formation of ulcers due to tissue irritation. As a result, these antrum-based devices under development have not been accepted by the medical community.

As can be seen from the above description of the problems and the state-of-the-art practices in the field of intragastric devices, a person of skill in the art would appreciate a gastric implant that (i) is more affordable for patients; (ii) is less feared by patients than obesity surgery; (iii) functions in the antrum region of the stomach to avoid limited treatment times associated with stomach expansion around current intragastric balloons; (iv) avoids passage of any part of the device past the pylorus to avoid retraction and entanglement in the stomach, ulcers, and passage of infectious materials into the duodenum; (v) is free floating in the stomach to avoid problems associated with fixation of the device, as well as promote normal gastric function; and, (vi) can be at least substantially leakproof when compared to state-of-the-art intragastric balloons.

SUMMARY

The teachings provided herein are directed to a high specific gravity intragastric device, a method for delivering the device in a subject, and a method for treating obesity in the subject. In many embodiments, the devices have an in vivo specific gravity ranging from about 1.2 g/ml to about 2.1 g/ml. In some embodiments, the teachings include an untethered, high specific gravity, antrum-based, intragastric device. The device can comprise an expandable casing having a biocompatible outer surface and, upon expansion, a predetermined shape for contacting the antrum of the stomach of a subject. The expanded casing can have a minimum, cross-sectional dimension of at least about 40 mm during operation of the device in the subject to avoid passage of any portion of the device through the lower esophageal sphincter or pyloric sphincter of the subject after expansion. The maximum, cross-sectional dimension of the predetermined shape can be about 80 mm for a positioning of the predetermined shape in the pyloric antrum of the subject. In these embodiments, the device includes a high specific gravity material, wherein the high specific gravity material contributes to an in vivo specific gravity of the device that ranges from about 1.2 g/ml to about 2.1 g/ml. It should be appreciated that the specific gravity of the device in vivo functions to direct the device to the pyloric antrum of the subject during use of the device.

In some embodiments, the intragastric device can comprise a flexible and expandable bladder having a biocompatible outer surface. Upon expansion, the bladder can have a predetermined shape for contacting the antrum of the stomach of a subject. The device can further comprise a means for expanding the bladder in vivo. And, in these embodiments, the flexible bladder can have a diameter upon expansion that ranges from about 40 mm to about 80 mm, as well as a high specific gravity material. The high specific gravity material can contribute to an in vivo specific gravity of the device that ranges from about 1.2 g/ml to about 2.1 g/ml to direct the device to the pyloric antrum of the subject during use of the device.

In some embodiments, the bladder can have a fillable inner volume, and the means for expanding the bladder can include a sealable port that is incorporated in the bladder and in communication with the inner volume of the bladder. In some embodiments, the bladder can have a predetermined shape designed to apply a pressure to the pyloric antrum to satiate hunger in the subject.

The teachings are also directed to an untethered, high specific gravity, hydrogel-containing, intragastric device. The device can comprise an expandable casing having a biocompatible outer surface, an inner compartment, and a sealable port in communication with the inner compartment for expanding the casing in vivo. The casing can have a minimal dimension ranging from about 40 mm to about 80 mm during operation of the device in a subject to avoid passage of any portion of the device through the lower esophageal sphincter or pyloric sphincter of the subject. Moreover, the casing can also have an aspect ratio ranging from about 1:1 to about 2:1 during operation. The device also comprises a high specific gravity material, wherein the high specific gravity material contributes to a specific gravity of the device during use that ranges from about 1.2 g/ml to about 2.1 g/ml, wherein the specific gravity functions to direct the device to the antrum of the stomach of the subject during use of the device. Moreover, in some embodiments, the intragastric device comprises a hydrogel material.

The teachings are also directed to an untethered, high specific gravity, antrum-based, intragastric device that is substantially leakproof. The device can include an expandable casing having a biocompatible outer surface and, upon expansion, a predetermined shape for contacting the antrum of the stomach of a subject. In these embodiments, the expanded casing can have a minimum, cross-sectional dimension of at least about 40 mm during operation of the device in the subject to avoid passage of any portion of the device through the lower esophageal sphincter or pyloric sphincter of the subject after expansion. Moreover, the expanded casing can have a maximum, cross-sectional dimension of the predetermined shape of about 80 mm for a positioning of the predetermined shape in the pyloric antrum of the subject. A filling material can be used to expand the casing and can comprise a biocompatible fluid component and a hydrogel component, wherein the filling material makes the device substantially leakproof and contributes to an in vivo specific gravity of the device that ranges from about 1.2 g/ml to about 2.1 g/ml, the specific gravity functioning to direct the device to the pyloric antrum of the subject during use of the device.

The teachings are also directed to an intragastric device comprising a flexible and expandable bladder having a predetermined shape upon expansion for contacting the antrum of the stomach of a subject. The device can be designed to avoid passage of any part of the device beyond the pylorus and lower esophageal sphincter while the bladder is expanded during use in vivo. In these embodiments, the bladder can contain a high specific gravity material when expanded; wherein, the high specific gravity material contributes to an in vivo specific gravity of the device that ranges from about 1.2 g/ml to about 2.1 g/ml and functions to direct the device to the pyloric antrum of the subject during use of the device. Moreover, these embodiments can include a filling material comprising a biocompatible fluid component and a hydrogel component, wherein the filling material makes the device substantially leakproof and contributes to the in vivo specific gravity of the device.

In some embodiments, the casing comprises the high specific gravity material whereas, in some embodiments, the outer surface of the casing comprises the high specific gravity material. In some embodiments, the casing encloses an inner compartment and has a sealable port in communication with the inner compartment for administering a fluid and expanding the casing in the stomach of a subject. And, in some embodiments, the inner compartment contains the high specific gravity material. Moreover, in some embodiments, the inner compartment contains the high specific gravity material, and the high specific gravity material is integrated with the casing.

In some embodiments, the intragastric device comprises an inner compartment. The inner compartment can contain the high specific gravity material, the casing can comprise the high specific gravity material, the high specific gravity material can be contained by the inner compartment and integrated with the casing, the outer surface of the casing can comprise the high specific gravity material, or a combination thereof.

The high specific gravity material, for example, can comprise a biocompatible fluid. And, in some embodiments, the high specific gravity material can comprise a biocompatible fluid selected from the group consisting of a salt solution, a sugar solution, honey, a sugar alcohol solution, glycerin, or a combination thereof.

The high specific gravity material can comprise a solid component. In some embodiments, expansion of the solid component contributes to expansion of the casing. And, in some embodiments, the high specific gravity material can comprise a solid component that is hygroscopic. In fact, in some embodiments, the high specific gravity material comprises a hydrogel. Some solid component can be selected to make the device substantially leakproof, for example, where the solid component comprises a hydrogel.

In some embodiments, the high specific gravity material can comprise a biocompatible solid selected from the group consisting of a metal, a salt, a heavy polymer, or a combination thereof.

The specific gravity of the devices taught herein as deployed in vivo is preselected to direct the device to the antrum of the stomach during use. For example, the device can have an in vivo specific gravity ranging from about 1.2 g/ml to about 2.1 g/ml, from about 1.2 g/ml to about 1.5 g/ml, from about 1.2 g/ml to about 1.3 g/ml, from about 1.3 g/ml to about 1.6 g/ml, or any range therein.

The outer surface of the devices taught herein should not irritate the stomach lining and, in many embodiments, the outer surface is smooth. In some embodiments, a portion of the outer surface is compliant or substantially compliant with a surface of the antrum and has a durometer of at least about Shore 40A.

The devices taught herein can have the added feature of satiating hunger in a subject during treatment. For example, in some embodiments, the device can have a predetermined shape, wherein the predetermined shape can be designed to apply a pressure to the antrum to satiate hunger in the subject.

The devices taught herein can be designed to include an antimicrobial agent. In some embodiments, for example, the expanded casing can contain an antimicrobial agent. And, in some embodiments, the filling material used to expand the device in vivo can include an antimicrobial agent.

The devices taught herein can be designed to be highly resistant to gastric acids to increase the longevity of the device, for example. In some embodiments, at least a portion of the outer surface is composed of a material comprising a gastric-acid resistant material.

The devices taught herein can be at least substantially leakproof. In some embodiments, the intragastric device is at least substantially leakproof, such that it functions to provide a volume sufficient to avoid passage of any portion of the device through the lower esophageal sphincter or pyloric sphincter of the subject for a period of at least 9 months.

The devices taught herein can be monitored non-invasively in vivo. In some embodiments, the intragastric device can have a casing that comprises an ultrasonically visible marker for ultrasonically monitoring the device in vivo.

The teachings are also directed to methods of administering the devices taught herein. The methods include placing the device in a collapsed state in the stomach of the subject; and, expanding the device after the placing; wherein, the high specific gravity functions to direct the device to the antrum of the stomach.

The teachings are also directed to methods of treating obesity in a subject using the devices taught herein. The methods include placing the device in a collapsed state in the stomach of the subject, expanding the device, and treating the subject for an effective amount of time. In some embodiments, the treating includes a deployment period of at least 9 months.

The teachings are also directed to kits that include the devices taught herein, as well as a filling material having a specific gravity of greater than 1.2 g/ml, and an insertion catheter designed for administration of the devices in a subject.

One of skill reading the teachings that follow will appreciate that the concepts can extend into additional embodiments that go well-beyond a literal reading of the claims, the inventions recited by the claims, and the terms recited in the claims.

BRIEF DESCRIPTION OF THE FIGURES

FIGS. 5A and 5B illustrate cross-sections of devices taught herein, wherein the devices have ultrasonically visible markings, in addition to different means for providing a high specific gravity material, according to some embodiments.

FIGS. 6A-6C illustrate ellipsoid, spherical, and pear-shaped devices, according to some embodiments.

DETAILED DESCRIPTION OF THE INVENTION

The teachings provided herein are directed to a high specific gravity intragastric device, a method for delivering the device in a subject, and a method for treating obesity in the subject. In many embodiments, the devices have an in vivo specific gravity ranging from about 1.2 g/ml to about 2.1 g/ml.

Figure 1:
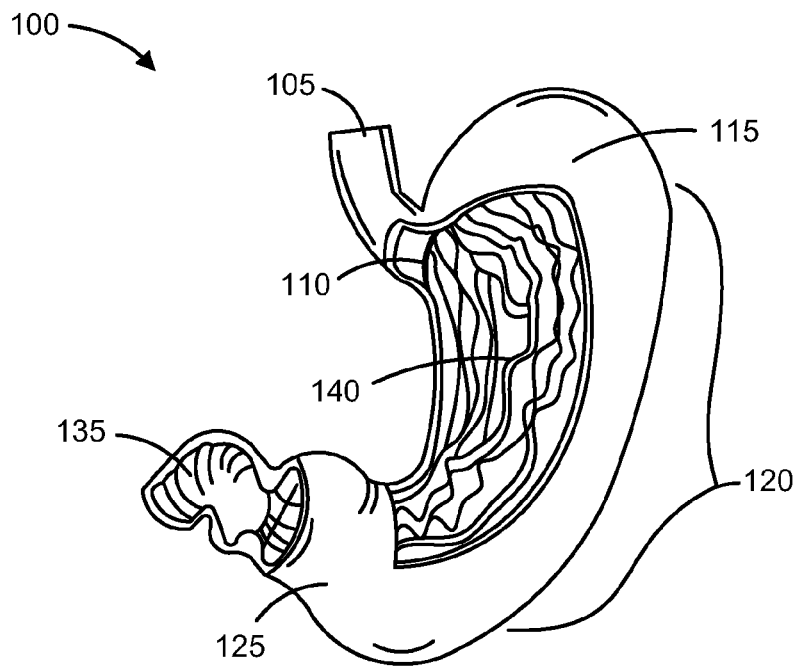
FIG. 1 illustrates the anatomy of a stomach, as described in some embodiments.

The devices are deployed in the stomach using methods known to one of skill. FIG. 1 illustrates the anatomy of a stomach, as described in some embodiments. Several features of the stomach 100 will be discussed in this application repeatedly. The stomach 100 is the region of the gastrointestinal tract between the esophagus 105 and the duodenum 135, where the stomach 100 is separated from the esophagus 105 and the duodenum 135 by the lower esophageal sphincter 110 and the pyloric sphincter 130 (aka the pylorus). The esophagus 105 carries food and drink to the stomach 100 through the lower esophageal sphincter 110. The stomach can be described in regions that include, for example, the fundus 115, the body 120, and the pyloric antrum 125 (aka the antrum). The volume of the stomach 100 can range tremendously. For example, the volume of the stomach 100 can range from about 45 ml when empty to about 1.5 L when full. After food and drink enter the stomach 100 through the lower esophageal sphincter 110, the stomach 100 contracts and churns its contents to assist in breaking down the contents for digestion. The stomach lining 140 can be irritated by the contents of the stomach 100 through the contracting and churning, resulting in discomfort and ulcers.

Figure 2:
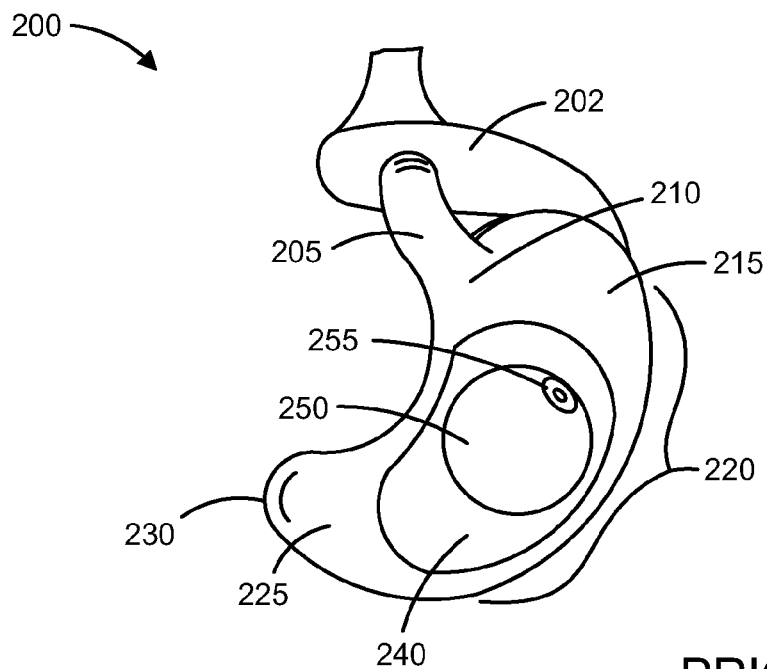
FIG. 2 illustrates a state-of-the-art intragastric balloon, over which the teachings provided herein contribute a number of improvements.

The intragastric balloon has been an intragastric device that has shown some considerable success in treating obesity. FIG. 2 illustrates a state-of-the-art intragastric balloon, over which the teachings provided herein contribute a number of improvements. The stomach 200 shows the same features of FIG. 1 beyond the diaphragm 202, including the esophagus 205, lower esophageal sphincter 210, fundus 215, body 220, antrum 225, pylorus 230, and lining 240. FIG. 2 shows a current state-of-the-art BioEnterics Intragastric Balloon (BIB) device 250 positioned to be free-floating in the upper region of stomach 200, in the region of the body 220 and fundus 215, where the stomach tissue can expand and adapt to the added volume of the BIB device 250 over time. The BIB device 250 also shows a filling valve 255 through which the BIB device 250 is expanded after delivering the device 250 to the stomach 200 of a patient.

The present teachings provide several improvements over the BIB device and are directed to an antrum-based, intragastric device. In some embodiments, the teachings include an untethered, high specific gravity, antrum-based, intragastric device comprising an expandable casing having a biocompatible outer surface. Upon expansion, the device has a predetermined shape for contacting the antrum of the stomach of a subject, a region of the stomach that is much more muscular than the body and fundus. The antrum is much less likely to stretch to accommodate the presence of the device, thus resulting in a longer lasting therapeutic effect in the subject, as well as less post-placement symptoms that include, but are not limited to, vomiting. The expanded casing can have a minimum, cross-sectional dimension of at least about 40 mm during operation of the device in the subject to avoid passage of any portion of the device through the lower esophageal sphincter or pyloric sphincter of the subject after expansion. The maximum, cross-sectional dimension of the predetermined shape can be about 80 mm for a positioning of the predetermined shape in the pyloric antrum of the subject. In these embodiments, the device includes a high specific gravity material, wherein the high specific gravity material contributes to an in vivo specific gravity of the device that ranges from about 1.2 g/ml to about 2.1 g/ml. It should be appreciated that the specific gravity of the device in vivo functions to direct the device to the pyloric antrum of the subject during use of the device. It should also be appreciated that the use of the device includes filling of the stomach at a mealtime, such that the specific gravity of the device in vivo functions to direct the device to the pyloric antrum of the subject during the filling of the stomach at mealtime.

It should be appreciated that the "expandable casing" of the devices taught herein can be elastomeric or non-elastomeric. The expansion of the casing can occur using any method known to one of skill including, but not limited to an expansion that is hydraulic, pneumatic, mechanical, or a combination thereof. In some embodiments, the expansion can occur using a fluid, and the fluid can be a gas or a liquid. The liquid can be aqueous or non-aqueous. In most embodiments, the fluid should be biocompatible. In some embodiments, the expansion can include a mechanical method such as, for example, through the use of a scaffolding mechanism.

The term "biocompatible" can generally refer to a material that does not cause substantial injury, or an otherwise substantially toxic or immunologic reaction to the tissue of the patient. The term "substantially" can refer to a condition in which one of skill in the art would consider to be a meaningful or considerable state or change of states. A substantial injury could include an injury that considerably changed the tissue of a patient, for example, such that additional medical care may be needed, or is needed, to remedy the injury. Likewise a substantially toxic or immunologic reaction could include a reaction that should not, or cannot, be overlooked in a treatment program. The devices taught herein, for example, can be designed to have smooth, outer surfaces that prevent or inhibit irritation of the stomach lining during a treatment period. Or, likewise, do not cause an abrasive action on the device, whether from the stomach lining or the device itself, that could accelerate failure of the device leading to leakage or collapse in a subject during treatment. Such an outer surface could be considered biocompatible, as it prevents or inhibits the likelihood of a direct injury due to a stomach lining irritation or an indirect injury that may occur from a failure of the device, such as an intestinal blockage from the device potentially lodging in the intestinal tract after failure. It should also be appreciated that "contacting the antrum" includes a periodic contact, since embodiments taught herein are directed to free-floating devices to allow for normal gastric function.

Figure 3:
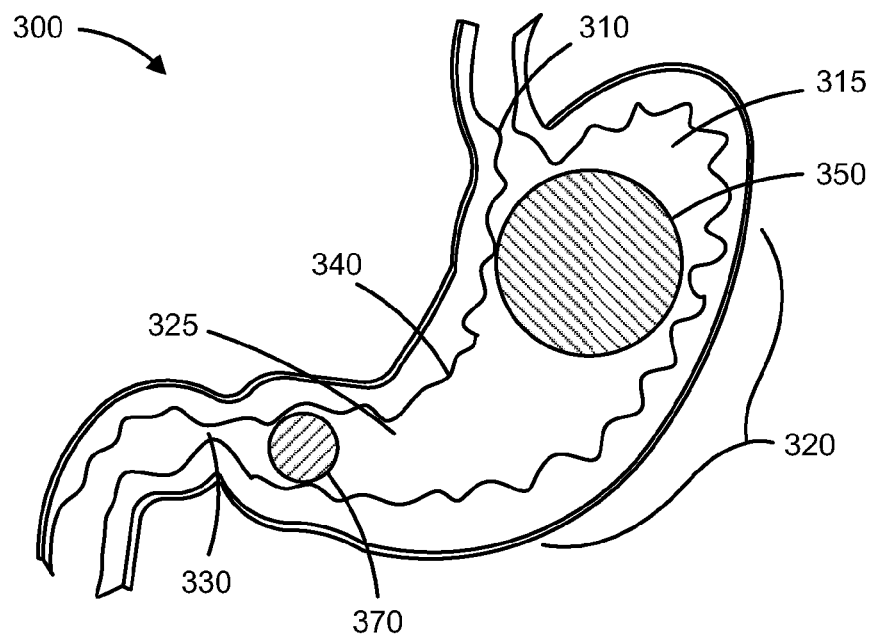
FIG. 3 illustrates where a state-of-the-art intragastric balloon functions in the stomach, as compared to a device taught herein, according to some embodiments.

The state-of-the-art devices described above differ in many ways from the devices taught herein, including the location where the devices function in the stomach. FIG. 3 illustrates where a state-of-the-art intragastric balloon functions in the stomach, as compared to a device taught herein, according to some embodiments. Stomach 300 shows the features of the stomach described above, including the lower esophageal sphincter 310, the fundus 315, the body 320, the antrum 325, the pylorus 330, and the lining 340.

A current, state-of-the-art intragastric balloon 350 can be seen as free-floating around the body and fundus of the stomach, and an antrum-based device 370 as taught herein can be seen as free-floating in the stomach 300 in a position as distal as the antrum 325. The state-of-the-art balloon 350 cannot free-float in the antrum for at least two reasons: it's too large, having a volume that ranges from about 400 ml to about 800 ml, usually around 550 ml; and, its specific gravity makes it too buoyant to travel to the antrum 325 through the stomach contents. The antrum-based device taught herein is smaller, having a minimum, cross-sectional dimension of at least about 40 mm during operation of the device in a subject to avoid passage of any portion of the device through the lower esophageal sphincter 310 or pyloric sphincter 330 of the subject after expansion; and a maximum, cross-sectional dimension of about 80 mm for a positioning of the antrum-based device 370 in the pyloric antrum of the subject. Moreover, the antrum-based device 370 as taught herein has a high specific gravity material that contributes to an in vivo specific gravity of the device that ranges from about 1.2 g/ml to about 2.1 g/ml, the high specific gravity functioning to direct the device to the pyloric antrum of the subject during a treatment.

In some embodiments, the intragastric device can comprise a flexible and expandable bladder having a biocompatible outer surface. Upon expansion, the bladder can have a predetermined shape for contacting the antrum of the stomach of a subject. The device can further comprise a means for expanding the bladder in vivo. And, in these embodiments, the flexible bladder can have a diameter upon expansion that ranges from about 40 mm to about 80 mm, as well as a high specific gravity material. The high specific gravity material can contribute to an in vivo specific gravity of the device that ranges from about 1.2 g/ml to about 2.1 g/ml to direct the device to the pyloric antrum of the subject during use of the device.

In some embodiments, the bladder can have a fillable inner volume, and the means for expanding the bladder can include a sealable port that is incorporated in the bladder and in communication with the inner volume of the bladder. In some embodiments, the bladder can have a predetermined shape designed to apply a pressure to the pyloric antrum to satiate hunger in the subject. Any sealable port known to one of skill can be used with the teachings provided herein. An example of sealable port is shown, for example, as the filling valve 255 shown in FIG. 2.

The devices taught herein can be substantially leakproof. In fact, the teachings provided herein can be used to improve the current, state-of-the-art devices, such as the fundus-based devices depicted by the examples in FIGS. 2 and 3. The term "substantially leakproof" can include devices that do not leak to the extent that they no longer provide a therapeutic result through a time frame of at least 9 months. In some embodiments, the devices do not leak to the extent that they no longer provide a therapeutic result through a time frame of 12 months, 18 months, 21 months, 24 months, 30 months, 36 months, 42 months, 48 months, or any range therein.

As such, the teachings can also be directed to any intragastric device comprising a flexible and expandable bladder having a predetermined shape upon expansion for contacting the antrum of the stomach of a subject. The device can be designed to avoid passage of any part of the device beyond the pylorus and lower esophageal sphincter while the bladder is expanded during use in vivo. In these embodiments, the bladder can contain a high specific gravity material when expanded; wherein, the high specific gravity material contributes to an in vivo specific gravity of the device that ranges from about 1.2 g/ml to about 2.1 g/ml and functions to direct the device to the pyloric antrum of the subject during use of the device. Moreover, these embodiments can include a filling material comprising a biocompatible fluid component and a hydrogel component, wherein the filling material makes the device substantially leakproof and can also contribute, in some embodiments, to the in vivo specific gravity of the device.

Each device can be designed with a different aspect ratio, and the aspect ratio of the device can be used as an additional design feature as an additional consideration for the predetermined shape of the device. As such, the teachings are also directed to an untethered, high specific gravity, hydrogel-containing, intragastric device. The device can comprise an expandable casing having a biocompatible outer surface, an inner compartment, and a sealable port in communication with the inner compartment for expanding the casing in vivo. The casing can have a minimal dimension of about 40 mm during operation of the device in a subject to avoid passage of any portion of the device through the lower esophageal sphincter or pyloric sphincter of the subject. And, the casing can also have an aspect ratio ranging from about 1:1 to about 2:1 during operation. The device also comprises a high specific gravity material, wherein the high specific gravity material contributes to a specific gravity of the device during use that ranges from about 1.2 g/ml to about 2.1 g/ml, the specific gravity functioning to direct the device to the antrum of the stomach of the subject during use of the device. The device can also comprise a hydrogel material as described herein.

The diameter of the device can range from about 40 mm to about 80 mm, in many embodiments. In some embodiments, the diameter can range from about 40 mm to about 75 mm, from about 45 mm to about 75 mm, from about 45 mm to about 65 mm, from about 55 mm to about 75 mm, about 65 mm, or any range therein. The diameter of the portion of the device that contacts the antrum portion of the stomach can be 40 mm, 45 mm, 50 mm, 55 mm, 60 mm, 65 mm, 70 mm, 75 mm, 80 mm, or any range therein. It should be appreciated that the diameter of the collapsed device should be less than 20 mm, in most embodiments, to allow the collapsed device to pass through the lower esophageal sphincter during placement and removal of the device in the subject.

The filling material can include a heavy fluid that contributes to the high specific gravity of the device. As such, the teachings are also directed to an untethered, high specific gravity, antrum-based, intragastric device that is substantially leakproof, the device having an expandable casing that includes a biocompatible outer surface and, upon expansion, a predetermined shape for contacting the antrum of the stomach of a subject. In these embodiments, the expanded casing can have a minimum, cross-sectional dimension of at least about 40 mm during operation of the device in the subject to avoid passage of any portion of the device through the lower esophageal sphincter or pyloric sphincter of the subject after expansion. Moreover, the expanded casing can have a maximum, cross-sectional dimension of the predetermined shape of about 80 mm for a positioning of the predetermined shape in the pyloric antrum of the subject. A filling material can be used to expand the casing and can comprise a biocompatible fluid component and a hydrogel component, wherein the filling material makes the device substantially leakproof and contributes to an in vivo specific gravity of the device that ranges from about 1.2 g/ml to about 2.1 g/ml, the specific gravity functioning to direct the device to the pyloric antrum of the subject during use of the device. As described above, the biocompatible fluid component can be a heavy fluid having a high specific gravity that contributes to the high specific gravity of the device.

Figure 4:
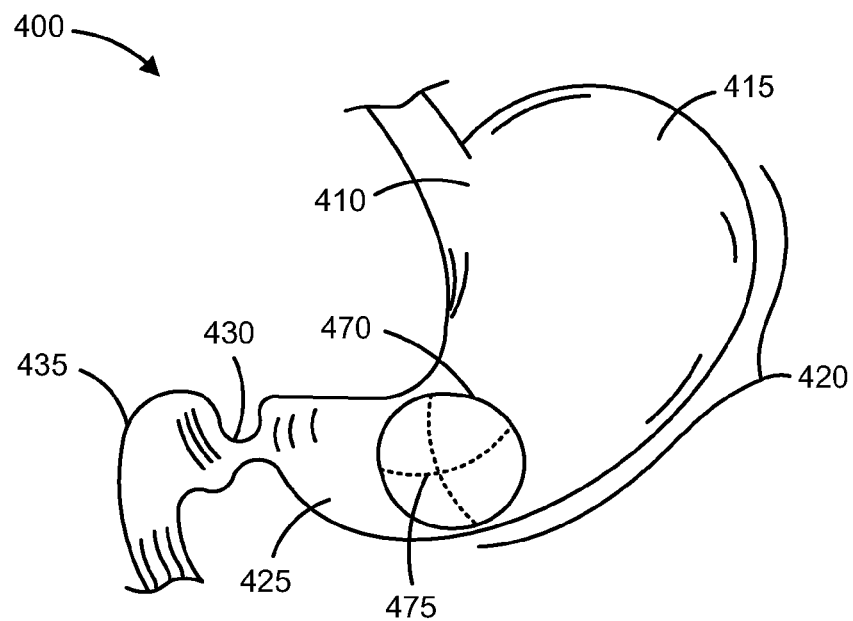
FIG. 4 illustrates a device taught herein and having ultrasonically visible markings, according to some embodiments.

The devices taught herein can be monitored non-invasively in vivo. In some embodiments, the intragastric device can comprise an ultrasonically visible marker for ultrasonically monitoring the device in vivo. And in some embodiments, the intragastric device can comprise a radio-opaque marker for monitoring the device using x-rays. FIG. 4 illustrates a device taught herein and having ultrasonically visible markings, according to some embodiments. The stomach 400 has the features described above, including the lower esophageal sphincter 410, the fundus 415, body 420, antrum 425, pylorus 430, and duodenum 435. The intragastric device 470, however, has ultrasonically visible markers 475 that allow a monitoring of the device during a treatment. In some embodiments, the marker can show the position of the device 470 in the stomach 400, the shape of the device 470 in the stomach 400, or a combination thereof.

It should be appreciated that the marker can be selected to facilitate the system used to monitor the intragastric device in the patient. Radio-opaque markers for use of an x-ray system in the monitoring could include, for example, a dense, solid material, such as a metal. An iodine-containing fluid, or a derivative thereof, is an example of a fluid that could be used. One of skill will appreciate the range of acceptable radio-opaque materials that would be suitable for use with the present teachings. Ultrasonically visible markers could include, for example, hollow polymeric spheres, gas-filled spheres, or the like. One of skill will appreciate the range of acceptable radio-opaque materials and ultrasonically visible materials that would be suitable for use with the present teachings. Moreover, the position of the markers on the intragastric device can assist in the visualization of the shape of the device in vivo. For example, the markers can be positioned to assist in the imaging of the change in shape of the device, where the change in shape could indicate a pressure induced on the device by the antrum of the stomach, or possibly a change in volume of the device due to leakage.

Any biocompatible, ultrasonically visible material can be used, and the material can be placed in any size, number, or position that one of skill would believe is operable in view of the teachings herein. For example, the ultrasonically visible material can be a solid line, a series of dashed lines, and/or circumscribe at least one circumference of the device. High specific gravity particles or pellets can be used, in some embodiments, as long as they are adequately visible using ultrasound. Likewise, dyes can be used to help identify leakage of the device. The dyes can have a color that is visualized when expelled from the intestinal tract, or the dye can be radio-opaque for visualization using x-rays.

Any number of marker positions and shapes can be contemplated by one of skill. In some embodiments, the marker is an ultrasonically visible ring or set of rings that circumscribe the device. In some embodiments, the device is a sphere or an ellipsoid, and two rings circumscribe the device, wherein the rings are concentric and lie on orthogonal planes as shown in FIG. 4, markers 475.

The high specific gravity material can be located anywhere on or in the intragastric device, and its preferred location will depend on the embodiment. In some embodiments, the casing comprises the high specific gravity material whereas, in some embodiments, the outer surface of the casing comprises the high specific gravity material. In some embodiments, the casing encloses an inner compartment and has a sealable port in communication with the inner compartment for administering a fluid and expanding the casing in the stomach of a subject. And, in some embodiments, the inner compartment contains the high specific gravity material. Moreover, in some embodiments, the inner compartment contains the high specific gravity material, and the high specific gravity material is integrated with the casing. For example, the intragastric device can have a central column of high specific gravity particles, such as small tungsten spheres, for example, and the central column is integral to the internal casing. The process of integrating the column to the device can occur during the molding of the casing, such as in an injection molding process, or the column can be later attached using any method known to one of skill.

In some embodiments, the intragastric device comprises an inner compartment. The inner compartment can contain the high specific gravity material, the casing can comprise the high specific gravity material, the high specific gravity material can be contained by the inner compartment and integrated with the casing, the outer surface of the casing can comprise the high specific gravity material, or a combination thereof.

It should be appreciated that the high specific gravity material or component should collapse with the device and result in a collapsed device of no more than about 20 mm in diameter to allow for passage of the device through the lower esophageal sphincter. As a result, the size of the high specific gravity material is limited by this consideration.

Any combination of the teachings provided above can be used to design a device taught herein. For example, the device can have an ultrasonically visible marking and a particular placement of a high density solid material. FIGS. 5A and 5B illustrate cross-sections of devices taught herein, wherein the devices have ultrasonically visible markings, in addition to different means for providing a high specific gravity material, according to some embodiments. Intragastric device 570 includes a casing (or bladder) 505, an integrated high specific gravity component 560 that carries or contains a high specific gravity material 565, an ultrasonically visible marker 575 that circumscribes the device for monitoring the device in vivo, and a sealable port 590. FIG. 5A shows a high specific gravity component 560 that is integrated with the casing, where the component 560 can be part of the molding process for the casing (or bladder) 505 or a separate component attached to the casing using any means known to one of skill for attaching similar or dissimilar materials. FIG. 5B shows a high specific gravity material 565 integrated with the casing in a more embedded manner. Any method of integrating the high specific gravity material 565 suitable for application of the present teachings can be used, and such methods can be readily contemplated by one of skill.

The combinations of a predetermined shape, position of a high specific gravity component, selection of high specific gravity materials, and the like, can be highly variable. It should be appreciated that several device shapes can be contemplated by one of skill as a predetermined shape for use with the teachings provided herein. In some embodiments, the predetermined shapes can include a sphere, an ellipsoid, a pear-shaped configuration, a cylinder, and the like. FIGS. 6A-6C illustrate ellipsoid, spherical, and pear-shaped devices, according to some embodiments.

The high specific gravity material, for example, can comprise a biocompatible fluid. The fluid component can be a gas or a liquid in some embodiments, and can be positioned in the device in virtually any desired shape, size, number, or position in the device that's deemed operable to one of skill in view of the teachings provided herein. And, in some embodiments, the high specific gravity material can comprise a biocompatible fluid selected from the group consisting of a salt solution, a sugar solution, honey, a sugar alcohol solution, glycerin, or a combination thereof. Examples of a high specific gravity sugar alcohol include, but are not limited to, xylitol, sorbitol, and mannitol. In some embodiments, a 67 g sample of xylitol can be added to 100 g of water to provide a heavy fluid having a density of about 1.21 g/ml. An added benefit of the sugar alcohols is that they can serve as a good indicator of a leaking device, causing diarrhea upon leakage or failure of the device. In some embodiments, a liquid laxative can be heavy enough to be used as a high specific gravity filling material. Likewise, a laxative can serve as a good indicator of leakage by creating an intestinal response upon leakage or failure of the device. In some embodiments, some syrups can be used as a good filling material due to their high specific gravity. An example of a useful syrup is corn syrup, which can have a specific gravity of about 1.48 g/ml, in some embodiments. And, it should be appreciated that, in most embodiments taught herein, a combination of any of the materials set-forth herein can be used to compose the high specific gravity material of the intragastric device such as, for example, a combination of a metal ballast material and a high specific gravity fluid. In some embodiments, a hydrogel can be added to provide substantial leak resistance to the device.

The high specific gravity material, for example, can comprise a solid component. The solid component can be in virtually any desired shape, size, number, or position in the device that's deemed operable to one of skill in view of the teachings provided herein. In some embodiments, the solid component can include spheres, cylinders, liners, coatings, or particles. For example, the solid component can be a material such as tungsten, silver, or a stainless steel. In some embodiments, the solid component can include an encased material, such as an epoxy-encased lead. In some embodiments, the solid component can be incorporated in a solid core-type structure within the device, adhered to the internal or external walls of the device, in the wall of the device, incorporated into ultrasonically detectable bands, float freely inside the device, or a combination thereof.

In some embodiments, the high specific gravity component can be a coated or encased metal, a high specific gravity silicone a suspension of tungsten in a fluid, or prepackaged device that incorporates the high specific gravity material in its construction. For example, the device can be formed as a single mold that incorporates the high specific gravity material as part of the manufacturing process, such as a liquid molding process, where the high specific gravity material is integral to the device. In some embodiments, the device can be filled by injecting a gelling polymer composition, wherein the polymeric composition gels in place in vivo to form a relatively firm device having a high specific gravity, a device that will not easily leak or collapse due to abrasion, puncture, tear, or valve failure, greatly reducing the risk of the device passing into intestinal tract beyond the pylorus. In some embodiments the polymer composition is a thermoreactive hydrogel filler that activates at body temperature. The gel-in-place compositions can be administered as a premixed composition to expand the device in vivo, or it can be placed in the device during manufacture and an aqueous fluid added to activate the composition in vivo. In these embodiments, the device can be removed endoscopically by puncturing the device and either chopping-up or suctioning away the internal gel material. And, in some embodiments, the gel can be a biodegradable material, can include a leak-detecting dye or a radio-opaque material, or a combination thereof. In some embodiments, the gel can include a soft silicone or a polyurethane elastomer. Moreover, in some embodiments, the device includes a detachable filling valve designed to facilitate gel removal in vivo.

In some embodiments, the high specific gravity material can comprise a solid component and, in some of these embodiments, an expansion of the solid component can contribute to expansion of the casing. And, in some embodiments, the high specific gravity material can comprise a solid component that is hygroscopic. In fact, in some embodiments, the high specific gravity material comprises a hydrogel such as, for example, a polyvinyl alcohol hydrogel. In some embodiments, the solid component can make the device substantially leakproof such as, for example, where the solid component comprises a hydrogel.

In some embodiments, the high specific gravity material can comprise a biocompatible solid selected from the group consisting of a metal, a salt, a heavy polymer, or a combination thereof. Examples of a heavy polymer can include, but are not limited to, polyvinylchloride having a specific gravity of about 1.4 g/ml or polyethyleneterephthalate having a specific gravity of about 1.37 g/ml.

The specific gravity of the devices taught herein as deployed in vivo is preselected to direct the device to the antrum of the stomach during use. In some embodiments, the specific gravity of the device will function to place the device and generally maintain the position of the device in the stomach, such that the device is self-placing, stays in the antrum while eating, and will not float above the gastric contents of the stomach as the stomach fills. In some embodiments, the specific gravity of the device will function such that the device can freely move about the distal stomach between meals so that normal gastric functions continue. The specific gravity of the device should not be so heavy as to completely block the pylorus or fix in one location where it can stretch the distal stomach walls. One of skill will appreciate that stretching of the distal stomach walls may lead to a desensitization of the pressure sensing effects of the antral walls or, perhaps, cause pressure-induced erosions or ulcers. In some embodiments, the device can have an in vivo specific gravity ranging from about 1.2 g/ml to about 2.1 g/ml, from about 1.2 g/ml to about 1.5 g/ml, from about 1.2 g/ml to about 1.3 g/ml, from about 1.3 g/ml to about 1.6 g/ml, or any range therein. In some embodiments, the in vivo specific gravity of the device can be 1.2 g/ml, 1.3 g/ml, 1.4 g/ml, 1.5 g/ml, 1.6 g/ml, 1.7 g/ml, 1.8 g/ml, 1.9 g/ml, 2.0 g/ml, 2.1 g/ml, 2.2 g/ml, 2.3 g/ml, 2.4 g/ml, 2.5 g/ml, 3.0 g/ml, or any range therein.

The outer surface of the devices taught herein should not irritate the stomach lining and, in many embodiments, the outer surface is smooth. In some embodiments, the outer surface of the device is slippery due to the application of hydrogels or slippery polymers, such as fluorosilicones or parylene coatings, in the manufacture of the device. Such devices will have a lower surface friction when contacting the stomach lining during use than other surfaces comprised of, for example, di-methyl silicones or uncoated polyurethane elastomer shell surfaces.

The device should be relatively firm in many embodiments, as compared to most state-of-the-art liquid- or air-filled intragastric balloons. The firmness can be created by selection of the material and/or thickness of the casing, balloon, or shell material; always filling the device to at least 100% capacity; or a combination thereof. A firm device (i) can have a greater delayed gastric emptying effect than softer, more pliable devices; (ii) can deter stomach muscles from squeezing or distorting the device into shapes that could become wedged in the pylorus or forced past the pylorus, thereby reducing risk of complications; (iii) can deter stomach muscles from tearing or otherwise causing a structure failure of the device; thereby increasing the useful life of the device; and (iv) can reduce the occurrence of folds or creases in the device, thereby reducing the occurrence of structural failures or gastric irritations from the folds or creases.

Due to the pressure sensing effects produced in the antrum of the stomach, the devices taught herein can have the added feature of satiating hunger in a subject during treatment. For example, in some embodiments, the device can have a predetermined shape, wherein the predetermined shape can be designed to apply a pressure to the antrum to satiate hunger in the subject. In some embodiments, a portion of the outer surface is compliant or substantially compliant with a surface of the antrum and has a durometer of at least about Shore 40A. In some embodiments, the compliant surface of the device has a hardness ranging from about 40A to about 80A, from about 40A to about 70A, from about 40A to about 60A, from about 40A to about 50A, from about 40A to about 45A, from about 40A to about 42A, or any range therein. In some embodiments the thickness of the casing, balloon, or shell material ranges from about 0.20 mm to about 2.0 mm, from about 0.25 mm to about 1.75 mm, from about 0.30 mm to about 1.5 mm, from about 0.40 mm to about 1.25 mm, from about 0.25 mm to about 1.0 mm, from about 0.25 mm to about 0.75 mm, from about 0.50 mm to about 1.0 mm, or any range therein. One of skill can select an appropriate wall thickness for a preselected wall material and durometer.

The devices taught herein can be designed to include an antimicrobial agent. In some embodiments, for example, the expanded casing can contain an antimicrobial agent. And, in some embodiments, the filling material used to expand the device in vivo can include an antimicrobial agent. The antimicrobial agent, in some embodiments, can include an antibacterial or antifungal agent. The agents can be in the shell, coated on the shell, or included in the filling material. In some embodiments, the antimicrobial can include silver, an antimicrobial drug, or food grade additives that include, but are not limited to, sulfites. The antimicrobial can be added to impede the colonization of the device in vivo by bacteria, fungus, or mold, in some embodiments. In some embodiments, the antimicrobial agent can reduce or prevent the occurrence of bad breath that may otherwise be present from the treatment.

The devices taught herein can be designed to be highly resistant to gastric acids to increase the longevity of the device, for example. In some embodiments, at least a portion of the outer surface is composed of a material comprising a gastric-acid resistant material. Examples of gastric-acid resistant materials can include, but are not limited to fluorosilicones or parylene. Fluorosilicone materials may include, for example, FVMQ. Perfluoroelastomers, such as FFKM, may be used in some embodiments. And, high density polyethylene can also make a good choice of material, where a very acid-resistant, non-elastomeric material is desired.

As described above, the devices taught herein, as well as some current, state-of-the-art devices, can be designed to be at least substantially leakproof. In some embodiments, the intragastric device is at least substantially leakproof when it functions to provide a volume sufficient to avoid passage of any portion of the device through the lower esophageal sphincter or pyloric sphincter of the subject for a period of at least 9 months, 12 months, 15 months, 18 months, 21 months, 24 months, 27 months, 30 months, 33 months, 36 months, 48 months, or any range therein.

Figure 7:
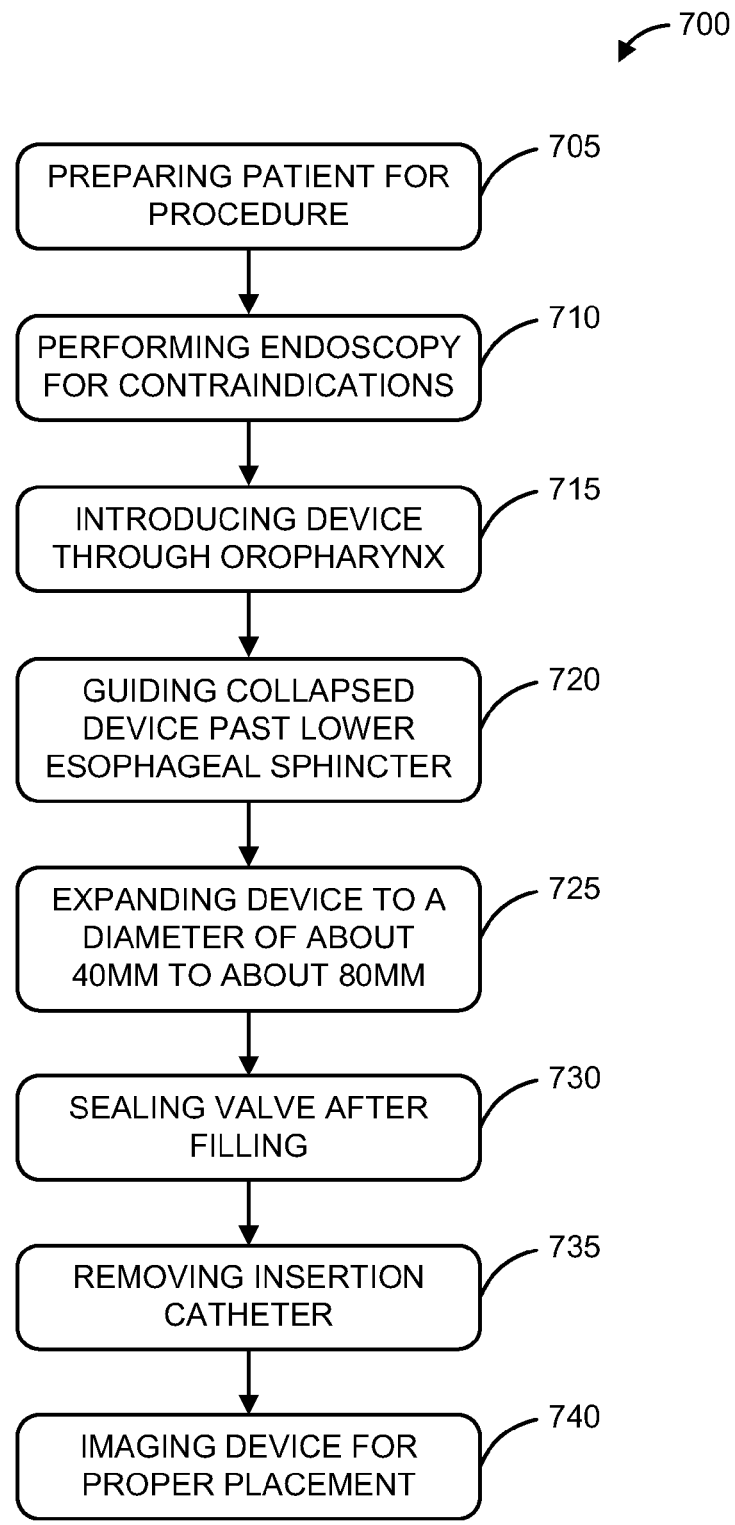
FIG. 7 provides a flowchart to describe a method of administering a device taught herein, according to some embodiments.

The teachings are also directed to methods of administering the devices taught herein. The methods include placing the device in a collapsed state in the stomach of the subject; and, expanding the device after the placing; wherein, the high specific gravity functions to direct the device to the antrum of the stomach. FIG. 7 provides a flowchart to describe a method of administering a device taught herein, according to some embodiments. The procedure 700 will often begin by preparing 705 the patient for the procedure. The patient can be placed in a supine position or left decubitus, a xylocalne spray can be applied to the oropharynx, and an intravenous sedation or general anesthesia can be administered in preparation for endoscopy. The next step can often include performing 710 endoscopy to identify contraindications that could be detrimental to the patient if the intragastric device is administered. The endoscopy is then followed by introducing 715 the collapsed device through the oropharynx of the patient, and guiding 720 the collapsed device past the lower esophageal sphincter. The next step the expanding 725 of the device to a diameter of about 40 mm to about 80 mm, sealing 730 the valve after filling the device, removing 735 the insertion catheter, and often imaging 740 the device to ensure proper placement in the stomach.

The teachings are also directed to methods of treating obesity in a subject using the devices taught herein. The methods include placing the device in a collapsed state in the stomach of the subject, expanding the device, and treating the subject for an effective amount of time. In some embodiments, the treating includes a deployment period of at least 9 months. An "effective amount" can be used to describe a therapeutically effective amount of time. A "therapeutically effective amount" refers to an amount of time necessary to achieve a desired therapeutic result, including any biological or medicinal response sought by a researcher, veterinarian, medical doctor or other clinician that may be part of a treatment plan. In one example, a therapeutically effective amount refers to the amount of a therapeutic agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the treatment.

The teachings are also directed to kits that include the devices taught herein, as well as a filling material having a specific gravity of greater than 1.2 g/ml, and an insertion catheter designed for administration of the devices in a subject. In some embodiments, the kits include instructions that alert the medical professional to contraindications, procedural considerations, and particularly topics of interest that are not common to the current, state-of-the-art intragastric devices. Such topics could include considerations relevant to the administration of various filling materials, such as the pressures and apparatus that may be required to inject the various filling materials, such as hydrogel materials, and the like. In some embodiments, the kits include the injection apparatus.

It should be appreciated that the devices taught herein can generally be easily adopted by the medical community. One of skill will appreciate that, in many embodiments, the methods of inserting and removing the devices, the types and uses of self-sealing fill valves, the weight loss programs, the introduction and removal catheters, and the instruments used with the intragastric device can be similar to those used with the current, state-of-the-art intragastric balloons.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

Relative Effect of Increasing Specific Gravity

This example compares a 1.0 g/ml specific gravity intragastric balloon sitting in a 1.0 g/ml water bath to the behavior of similar sized balloons having a specific gravity greater than that of the surrounding fluid bath.

Methods

Test samples having a Specific Gravity of 1.0 g/ml, 1.21 g/ml, 1.46 g/ml, 1.88 g/ml, and 2.07 g/ml were prepared from 75 cc latex balloons filled with distilled water, and adding steel pellets for ballast to increase the specific gravity to desired range.

The weight and displacement of each sample was measured after the balloons had been filled, air expelled and tied closed with a single knot. The targeted specific gravities were in range of 1.0 g/ml, 1.2 g/ml, 1.5 g/ml, 1.9 g/ml, and 2.1 g/ml. All quantitative measurements were taken at room temperature.

Step 1: Each sample was placed into the bottom of an empty, two liter open-top glass flask. One liter of tap water was added over a period of 3-5 seconds. Movement of the test sample was observed including motion around the base of the flask and motion above the base of the flask. The flask was gently swirled for 5 seconds and movement of the sample was recorded. The sample was removed and the test was repeated until all samples had been evaluated.

Step 2: Next, each sample was gently placed in two liters of tap water in the open flask that sat still on countertop, such that the tap water was initially motionless. Motion of the sample was observed and recorded, with the test repeated until all samples were evaluated.

Materials and Equipment:

Balloons: The latex balloons were 75 cc, round in shape, and the measured wall thickness averaged 0.3 mm around equator. The weight of the balloons was 3 grams each, and they were gray in color. One sample was prepared for each specific gravity level.

Ballast: Zinc plated, steel BB pellets were used. The pellets were 4.41 mm diameter, and 0.35 grams (Daisy, USA #7541) each. The pellets were added as needed to reach the desired specific gravity range of each sample. (Example: a 1.47 g/ml specific gravity sample was obtained from a balloon having a weight of 113 grams. 121 BB pellets were added to 70 cc water to get near the target of 1.5 g/ml specific gravity.)

Fill media: distilled water

Filling Mechanism: a 60 cc plastic syringe was used for filling samples; and a plastic funnel for transferring ballast into balloon.

Observation Container: a two liter flat bottomed clear glass flask (approximately 100 mm diameter×200 mm tall) was used to observe relative buoyancy.

Specific Gravity Measurements: an electronic weighing scale (Taylor Model 3831, SN: VO427) was used with a 400 cc graduated flask (10 mm graduations) for measuring displaced volume.

Table 1 provides the observations.

TABLE 1

| Sample | Specific Gravity | Step 1 - Submerge w/ Water | Step 2 - Place in Water |
|---|---|---|---|
| 1 | 1.0 | Floats up, spins in water | Floats freely below surface |
| 2 | 1.21 | Stays positioned at bottom, some rotation | Rapidly sinks to base, no motion (Striking difference from #1 reaction) |
| 3 | 1.46 | Stays positioned at bottom, some rotation | Rapidly sinks to base, no motion |
| 4 | 1.88 | Stays positioned at bottom, no rotation | Rapidly sinks to base, no motion |
| 5 | 2.07 | Stays positioned at bottom, no rotation, no movement | Instantly sinks to base, no motion, dropped quickly to bottom of flask |

Note:
the samples were washed with tap water and dried after the tests were completed, and all samples survived the test without leakage or destruction.

Discussion

This experiment clearly showed that a small increase in the specific gravity of a free balloon relative to the specific gravity of a surrounding fluid bath produced a striking difference in how the device behaves and how fast it can be expected to position itself at the bottom of a container.

The undesirable floating nature of the 1.0 g/ml sample was not surprising. But the progressive sinking effect observed from increasing the specific gravity of the test devices above 1.0 g/ml, and the stability of the device on the bottom of the observation container was more dramatic than anticipated. This was especially true when first observed with the 1.21 g/ml sample.

The 1.0 g/ml sample, in contrast to the others, did not place itself or stay on the bottom of the flask. This would indicate that any free floating intragastric device intended to stay positioned in the distal stomach should benefit greatly from a relative specific gravity that is greater than the specific gravity of the contents of a meal.

Example 2

Selection of the Specific Gravity of an Intragastric Device

This example shows the behavior of a variety of the intragastric devices in a variety of simulated meals. If meal contents are of a higher density than the intragastric device, the device will not likely be gravitationally directed to the distal stomach during feeding times. As such, the device will not likely act on the antral region, which makes it unlikely it will influence eating behavior by exerting pressure on the antrum walls.

The intragastric device needs to be relatively heavier than typical meal contents, but it should not be excessively heavy, as that might cause an injury, such as plugging up the outlet path from the stomach to the intestines, or possibly producing pressure on the gastric walls that leads to ulceration or pain.

The following results demonstrate that the specific gravity of many typical foods can be a bit higher than one might expect. The results provide the range of specific gravity within which the intragastric device will gravitationally position itself in the antral region during intake at meals and contact the antral walls.

Methods

Samples of fresh food that can be expected to be consumed by overweight patients were simulated to measure specific gravity both alone and when mixed in with other foods. Two simple meals were created. The effect of other fluids (hydrochloric acid secreted by the stomach (specific gravity approx. 1.07 g/ml) and saliva (specific gravity approx 1.01 g/ml) were not included for this exercise, as their effects were considered insubstantial for purposes of this study.

Five test samples from Example 1 (specific gravity of 1.0 g/ml, 1.21 g/ml, 1.46 g/ml, 1.88 g/ml, and 2.07 g/ml, approx. 75 cc each) were submerged in each of the sample meals and movement of the test samples was observed and recorded. All quantitative measurements were taken at room temperature.

Step 1: each sample was placed in the clear plastic food container, which sat still on the countertop. The breakfast meal was quickly poured over the top of the sample and the reaction of the test sample was observed from all sides of container for 30 seconds and observations recorded. The container was next gently swirled by hand in a circular pattern for 10 seconds and the reaction was recorded. The sample was removed and test was repeated until all samples had been evaluated.

Step 2: each sample was placed in the clear plastic food container, which sat still on the countertop. The spaghetti meal was quickly poured over the top of the sample and the reaction of the test sample was observed from all sides of container for 30 seconds and observations recorded. The container was next gently swirled by hand in a circular pattern for 10 seconds and reaction was recorded. Sample was removed from meal and was replaced and released gently on surface of meal within 30 seconds, and then all sides of container were observed for 30 seconds. Sample was removed and test was repeated until all samples had been evaluated. Observations recorded.

Materials and Equipment

The same balloons, ballast, fill media, and filling mechanism were used as described in Example 1.

Observation Container: a 1.4 Pint (approx 680 cc) Clear plastic food container, 110 mm wide, 110 mm long, 80 mm deep (Rubbermaid 15-378U).

Specific Gravity measurements: an electronic weighing scale (Taylor Model 3831, SN: V0427) was used with a 400 cc graduated flask (10 mm graduations) for measuring displaced volume.

Table 2 provides the composition and specific gravities (SG, g/ml) of the foods and meals prepared for testing.

TABLE 2

| Food/Meal | Brand | Preparation | Volume Ml | S.G. g/ml |
|---|---|---|---|---|
| Soft Drink | Coke Classic | As received | 200 | 1.05 |
| Chocolate Shake | McDonald's Triple Thick | As Received | 200 | 1.08 |
| Beer | Negra Modelo | As received | | 1.03 |
| Orange Juice | Tropicana Pure Premium | As received, shaken for 10 seconds before use. | 200 | 1.07 |
| Oatmeal | Quaker Oats, Old Fashioned | One cup water, .5 cup oats, boiled until thick. | 160 | 1.06 |
| Spaghetti | Barilla Spaghetti #5 | 50 gr. portion, dry. Boiled 10 minutes in water until soft | — | — |
| Spaghetti Sauce | Fracesco Rivaldi Traditional, Original Recipe | As received, mixed in package for two minutes by hand stirring before use. | 200 | 1.16 |
| Breakfast Meal, pourable | Orange juice & Oatmeal | Cook oatmeal per package instructions, 160 gr. mass. Add 100 gr. water & 160 gr. orange juice, mix into uniform mass | 400 | 1.05 |
| Spaghetti Meal, heavy-thick, with Beer | Spaghetti, Sauce, & Beer | Hand mix the boiled pasta & sauce - 135 gr. cooked pasta, 185 gr. sauce, chop by hand into <2 cm pieces. Add beer (approx 200 cc) until mix is at pourable consistency. | a thick, but pourable consistency. 460 | 1.09 |

Results

Step 1—Table 3 provides the observations of testing the buoyancy of the intragastric device in a breakfast meal.

TABLE 3

| Sample | Specific Gravity g/ml | Submerge Sample with Breakfast Meal | Swirl Breakfast Meal Around Sample |
|---|---|---|---|
| 1 | 1.0 | Sample floats to top <2 seconds | Sample floats about surface |
| 2 | 1.21 | Sample stays on bottom of container | Sample stays on bottom of container-visible thru bottom of container & does not float up |
| 3 | 1.46 | Sample stays on bottom of container | Sample stays on bottom of container-visible thru bottom of container & does not float up |
| 4 | 1.88 | Sample stays on bottom of container | Sample stays on bottom of container-visible thru bottom of container & does not float up |
| 5 | 2.07 | Sample stays on bottom of container | Sample stays on bottom of container-visible thru bottom of container & does not float up |

Step 2—Table 4 provides the observations of testing the buoyancy of the intragastric device in a spaghetti meal.

TABLE 4

| Sample | Specific Gravity g/ml | Submerge Sample with Spaghetti Meal | Swirl Breakfast Meal Around Sample, Remove Sample and Replace |
|---|---|---|---|
| 1 | 1.0 | Sample floats to top in 5 seconds | Sample stays on top, & will not sink into meal after placed on surface |
| 2 | 1.21 | Sample stays on bottom of container | Sample visible thru bottom of container, stays on bottom during swirl with little movement & sinks back to bottom in 2 seconds after placed on surface. |
| 3 | 1.46 | Sample stays on bottom of container | Sample visible thru bottom of container, stays on bottom during swirl with little movement, & sinks back to bottom quickly after placed on surface. |
| 4 | 1.88 | Sample stays on bottom of container | Sample visible thru bottom of container, during swirl with little movement & sinks back to bottom as soon as released on surface. |
| 5 | 2.07 | Sample stays on bottom of container | Sample visible thru bottom of container, during swirl without sliding or rotating. Sample sinks back to bottom very quickly as soon as released on surface. |

Note:
the samples were washed with tap water and dried with an absorbent cloth after the tests were completed in steps 1 and 2, and all samples survived the test without leakage or destruction.

Discussion

This experiment demonstrated that meal contents can have a specific gravity exceeding 1.05 g/ml during the intake portion of digestion, and it showed how meal content density and consistency acts on intragastric balloon models with specific gravity ranging from 1.0 g/ml to over 2.0 g/ml.

Interestingly, we again see that an intragastric device having a specific gravity of about 1.2 g/ml, the low end of the contemplated range, performs well. Such a device can sink down through both a watery and a thick simulated meal, and stay in place, even if it is disturbed with a swirling action. This will translate into a good margin of negative buoyancy that will insure that the intragastric device is positioned and stays in place at the distal stomach location where it can influence gastric intake.

The experiment also showed that devices with a specific gravity near the high end of about 2.0 g/ml appear to be more than capable of holding the intragastric device in place. However, the 1.2 g/ml device appears to have a good base specific gravity. Moreover, although higher specific gravities may find use in some embodiments, it is likely that a specific gravity of about 2.1 g/ml will serve as a practical and useful upper limit in many applications.

Example 3

Leak Resistance of Optional Fill Media

This example shows the leak resistance of devices that include the use of novel filling media and techniques. It has been demonstrated that an increased leak resistance can be provided by using a hydrogel fill formulation to expand the intragastric devices. Interestingly, this innovation can apply to current state of the art intragastric balloons, as well as the intragastric devices taught herein.

Intragastric balloon treatments can take an extended period of time. Reviews of intragastric balloon use in the medical literature often cite the deflation of devices before the intended treatment time is achieved. Typically, existing balloon-based devices cannot be left in place longer than about 6 months due to the likelihood of deflation, which can lead to the passage of the deflated device down into the intestinal tract and cause obstruction or other injury. As such, one of skill will appreciate having a device that resists deflation for an extended treatment time.

As described above, the intragastric devices can include different forms of hydrogels as means of reducing the chance of deflation due to leakage from a variety of causes known to one of skill. Such causes can include, but are not limited to pinholes in the outer shell, for example, that may develop over time. Another example of leakage can occur from backflow leakage across the filling valve. The presence of stomach acid, as well as the mechanical churning in the stomach, can cause many types of failures, for example. Hydrogels provide a nice filling alternative that can at least substantially prevent or reduce such leakage and potential structural failures. Solid-like and/or cohesive, non-flowing hydrogels fill formulations could lead to extending the time for safe treatment beyond the standard six months, providing patients an additional amount of time to reduce their weight and adopt new eating habits.

The objective of this experiment was to create small holes in the shell of three sample balloon devices and to then compare leak rates. Two samples featured optional hydrogel filling solutions and the third was inflated with water.

Methods

Three test samples were assembled for this experiment using the latex balloons described above, and all testing was done at room temperature.

Sample #1 was filled with distilled water, which has similar viscosity and density as 0.9% normal saline solution.

Sample #2 was filled with a two part, high consistency polyvinyl alcohol hydrogel that crosslinked in the balloon.

Sample #3 was filled with 50 each, 2.5 mm diameter dehydrated spheres of acrylic-acrylamide co-polymer followed by adding a hydrating sugar alcohol solution of xylitol to swell the spheres inside the balloon. (Xylitol crystals were added to distilled water, to create a 1.22 specific gravity liquid solution)

Each sample was filled to a volume of approximately 75 cc, with each sample being weighed after the balloons had been filled, all air had been expelled and the filling stem had been sealed closed with a single knot.

Simulated Damage to the Intragastric Device

Each test sample was squeezed by hand, inspected and weighed again to verify there were no pre-test leaks.

Each sample was then punctured in two places, about one cm apart, along the equator of the filled balloon. A 0.55 mm diameter steel pin with round, non cutting tip, penetrating to a depth of 8 to 10 mm, was used to make the punctures.

The punctured samples were again hand squeezed, inspected and then weighed again. Observations were recorded.

The punctured samples were then placed in a shallow pan with the punctured area aligned so it was at approximately 90 degrees of rotation from vertical. Test devices were each covered by a 1 kg static compression load, applied for 30 minutes. The static load was removed and the test samples were weighed and inspected within 2 minutes of the end of the test.

Materials and Equipment:

Latex balloons: same as in above examples. One sample prepared for each fill media.

Fill media: sample #1—distilled water; sample #2—polyvinyl alcohol, two part hydrogel solution (Steve Spangler Sciences, Englewood Colo.); and sample #3—(a) 50 each, 2.5 mm diameter acrylic-acrylamide co-polymer dried hydrogel spheres (Steve Spangler Sciences, Englewood Colo./M2 Polymer Technologies, West Dundee, Ill.); (b) Xylitol sugar alcohol powder dissolved in distilled water to create hydrating solution, 1.22 g/ml (Jarrow Formulas, Los Angeles Calif.-powder).

Filling Mechanism: a 60 cc plastic syringe was used for filling samples; and a plastic funnel for transferring the hydrogel spheres into the balloons.

Pressure Application: full size masonry bricks to provide static load, wrapped in polyethylene film; and a 2"×4"×24" long wooden board to serve as balancing fulcrum for adjusting static load to 1 kg+/−100 grams.

Leakage Collection: a TEFLON-coated pan was used to serve as fluid collection basin to hold test samples under static load compression.

Weight and Volume Measurement: an electronic weighing scale (Taylor Model 3831, SN: V0427) was used for weighing samples and setting static load for each sample, and a 400 cc graduated flask (10 mm graduations) was used for measuring displaced volume.

Results

Table 5 provides the observations of the leakage tests.

TABLE 5

| Sample | Pre-Puncture Fill Weight gm | Observation After Puncture And Manual Squeeze | Weight After Puncture & Squeeze gm | Weight After 30 min Under 1 KG Compression gm |
|---|---|---|---|---|
| 1 | 76 | Two visible leaks-spay | 74 | 42* |
| 2 | 77 | No leaking, but feel gel material at holes | 77 | 77 (No visible leaks) |
| 3 | 93 | Two wet spots, no continuous leak | 93 | 92 (No visible leaks) |

*Visible amount of fill fluid observed in catch pan. Total fluid loss in 30 minutes was 32 grams (42% of the total fill weight).

Discussion:

This experiment demonstrated that incorporating a hydrogel filling solution into an intragastric balloon device can result in a device that is substantially more resistant to leakage and collapse than using a filling media normally used in current, state-of-the-art devices, such as a saline filling media.

We claim:

1. An untethered, high specific gravity, antrum-based, intragastric device, comprising:
    a single expandable casing having a biocompatible outer surface and, upon expansion, a predetermined shape for contacting the antrum of the stomach of a subject; wherein,
    the expanded casing has
        a minimum, cross-sectional dimension of at least about 40 mm during operation of the device in the subject to avoid passage of any portion of the device through the lower esophageal sphincter or pyloric sphincter of the subject after expansion, limiting the intragastric device to a minimum volume of $\pi(40\text{ mm})^3/6$ or about 33 ml;
        a maximum, cross-sectional dimension of the predetermined shape of about 70 mm for a positioning of the predetermined shape in the pyloric antrum of the subject, limiting the intragastric device to a maximum volume of $\pi(70\text{ mm})^3/6$ or about 180 ml; and,
    a high specific gravity material, wherein the high specific gravity material has a specific gravity that is greater than 1.2 and contributes to an in vivo specific gravity of the device that ranges from about 1.2 to about 2.1, wherein the specific gravity functions to direct the device to the pyloric antrum of the subject to induce gastric discomfort during use of the device;
    wherein, the specific gravity of the device allows the device to move freely about the distal stomach and apply pressure to the antrum without otherwise affecting normal gastric function of the subject.

2. The device of claim 1, wherein the casing comprises the high specific gravity material.

3. The device of claim 1, wherein the outer surface of the casing comprises the high specific gravity material.

4. The device of claim 1, wherein the casing encloses an inner compartment and has a sealable port in communication with the inner compartment for administering a fluid and expanding the casing in the stomach of a subject.

5. The device of claim 4, wherein the inner compartment contains the high specific gravity material.

6. The device of claim 4, wherein the inner compartment contains the high specific gravity material, and the high specific gravity material is integrated with the casing.

7. The device of claim 1, wherein the high specific gravity material comprises a biocompatible fluid.

8. The device of claim 1, wherein the high specific gravity material comprises a biocompatible fluid selected from the group consisting of a salt solution, a sugar solution, honey, a sugar alcohol solution, glycerin, or a combination thereof.

9. The device of claim 1, wherein the high specific gravity material comprises a sugar alcohol solution.

10. The device of claim 1, wherein the high specific gravity material comprises a solid component.

11. The device of claim 1, wherein the high specific gravity material comprises a solid component, and an expansion of the solid component contributes to expansion of the casing.

12. The device of claim 1, wherein the high specific gravity material comprises a solid component that is hygroscopic.

13. The device of claim 1, wherein the high specific gravity material comprises a hydrogel.

14. The device of claim 1, wherein the high specific gravity material comprises a biocompatible solid selected from the group consisting of a metal, a salt, a heavy polymer or a combination thereof.

15. The device of claim 1, wherein the device has an in vivo specific gravity ranging from about 1.2 to about 1.5.

16. The device of claim 1, wherein the device has an in vivo specific gravity ranging from about 1.2 to about 1.3.

17. The device of claim 1, wherein the device has an in vivo specific gravity ranging from about 1.3 to about 1.6.

18. The device of claim 1, wherein a portion of the outer surface is compliant or substantially compliant with a surface of the antrum and has a durometer of at least about Shore 40A.

19. The device of claim 1, wherein, the predetermined shape is designed to apply a pressure to the antrum to satiate hunger in the subject.

20. The device of claim 1, wherein the expanded casing contains an antimicrobial agent.

21. The device of claim 1, wherein at least a portion of the outer surface is composed of a material comprising a gastric-acid resistant material.

22. The device of claim 1, wherein the casing comprises an ultrasonically visible marker for ultrasonically monitoring the device in vivo.

23. A method of administering the device of claim 1, comprising:
    placing the device in a collapsed state in the stomach of the subject; and,
    expanding the device after the placing; wherein,
    the high specific gravity functions to direct the device to the antrum of the stomach.

24. A method of treating obesity in a subject using the device of claim 1, wherein the method comprises:
    placing the device in a collapsed state in the stomach of the subject;
    expanding the device; and,
    treating the subject for an effective amount of time.

25. The method of claim 24, wherein, the treating includes a deployment period of at least 9 months.

26. A kit comprising the device of claim 1, a filling material having a specific gravity of greater than 1.2, and an insertion catheter designed for administration of the device in the subject.

27. An intragastric device, comprising:
    a single flexible and expandable bladder having a biocompatible outer surface and, upon expansion, a predetermined shape for contacting the antrum of the stomach of a subject; and,
    a means for expanding the bladder in vivo; wherein,
    the flexible bladder has
        a diameter upon expansion that ranges from about 40 mm to about 70 mm, limiting the intragastric device to a minimum volume of $\pi(40\text{ mm})^3/6$ or about 33 ml and a maximum volume of $\pi(70\text{ mm})^3/6$ or about 180 ml; and,
    a high specific gravity material, wherein the high specific gravity material has a specific gravity that is greater than 1.2 and contributes to an in vivo specific gravity of the device that ranges from about 1.2 to about 2.1 and functions to direct the device to the pyloric antrum of the subject to induce gastric discomfort during use of the device;
    wherein, the specific gravity of the device allows the device to move freely about the distal stomach and apply pressure to the antrum without otherwise affecting normal gastric function of the subject.

28. The device of claim 27, wherein the bladder has a predetermined shape designed to apply a pressure to the pyloric antrum to satiate hunger in the subject.

29. The device of claim 27, wherein the device has an in vivo specific gravity ranging from about 1.3 to about 1.6.

30. The device of claim 27, wherein the device has an in vivo specific gravity ranging from about 1.2 to about 1.3.

31. The device of claim 27, wherein a portion of the outer surface is compliant or substantially compliant with a surface of the antrum and has a durometer of at least about Shore 40A.

32. The device of claim 27, wherein the casing comprises an ultrasonically visible marker for ultrasonically monitoring the device in vivo.

33. A method of administering the device of claim 27, comprising:
placing the device in a collapsed state in the stomach of the subject; and,
expanding the device after the placing; wherein,
the high specific gravity functions to direct the device to the antrum of the stomach.

34. A method of treating obesity in a subject using the device of claim 27, wherein the method comprises:
placing the device in a collapsed state in the stomach of the subject;
expanding the device; and,
treating the subject for an effective amount of time.

35. The method of claim 34, wherein, the treating includes a deployment period of at least 9 months.

36. A kit comprising the device of claim 27, a filling material having a specific gravity of greater than 1.2, and an insertion catheter designed for administration of the device in the subject.

37. An untethered, high specific gravity, hydrogel-containing, intragastric device that is at least substantially leakproof, wherein the device comprises:
a single having a biocompatible outer surface, an inner compartment, and a sealable port in communication with the inner compartment for expanding the casing in vivo; wherein, the casing has
a dimension ranging from a minimum of about 40 mm to a maximum of about 70 mm during operation of the device in a subject to avoid passage of any portion of the device through the lower esophageal sphincter or pyloric sphincter of the subject, limiting the intragastric device to a minimum volume of $\pi(40 \text{ mm})^3/6$ or about 33 ml and a maximum volume of $\pi(70 \text{ mm})^3/6$ or about 180 ml; and,
an aspect ratio ranging from about 1:1 to about 2:1 during operation of the device;
a high specific gravity material, wherein the high specific gravity material has a specific gravity that is greater than 1.2 and contributes to a specific gravity of the device during use that ranges from about 1.2 to about 2.1, wherein the specific gravity functions to direct the device to the antrum of the stomach of the subject to induce gastric discomfort during use of the device; and,
a hydrogel material;
wherein,
the intragastric device is at least substantially leakproof, functioning to provide a volume sufficient to avoid passage of any portion of the device through the lower esophageal sphincter or pyloric sphincter of the subject for a period of at least 9 months; and,
the specific gravity of the device allows the device to move freely about the distal stomach and apply pressure to the antrum without otherwise affecting normal gastric function of the subject.

38. The device of claim 37, wherein the device has an in vivo specific gravity ranging from about 1.3 to about 1.6.

39. The device of claim 37, wherein the device has an in vivo specific gravity ranging from about 1.2 to about 1.3.

40. The device of claim 37, wherein the inner compartment contains the high specific gravity material.

41. The device of claim 37, wherein the casing comprises the high specific gravity material.

42. The device of claim 37, wherein the high specific gravity material is contained by the inner compartment and integrated with the casing.

43. The device of claim 37, wherein the outer surface of the casing comprises the high specific gravity material.

44. The device of claim 37, wherein at least a portion of the outer surface is composed of a material comprising a gastric-acid resistant, low friction material.

45. The device of claim 37, wherein the device further comprises a surface that is compliant or substantially compliant with a surface of the antrum.

46. The device of claim 37, wherein a portion of the outer surface is compliant or substantially compliant with a surface of the antrum having a durometer of at least about Shore 40A.

47. The device of claim 37, wherein the casing comprises an ultrasonically visible marker for ultrasonically monitoring the device in vivo.

48. A method of administering the device of claim 37, comprising:
placing the device in a collapsed state in the stomach of the subject; and,
expanding the device after the placing; wherein,
the high specific gravity functions to direct the device to the antrum of the stomach.

49. A method of treating obesity in a subject using the device of claim 37, wherein the method comprises:
placing the device in a collapsed state in the stomach of the subject;
expanding the device; and,
treating the subject for an effective amount of time.

50. The method of claim 49, wherein, the treating includes a deployment period of at least 9 months.

51. A kit comprising the device of claim 37, a filling material having a specific gravity of greater than 1.2, and an insertion catheter designed for administration of the device in the subject.

52. An untethered, high specific gravity, antrum-based, intragastric device, comprising:
a single expandable casing having a biocompatible outer surface and, upon expansion, a predetermined shape for contacting the antrum of the stomach of a subject; wherein,
the expanded casing has
a minimum, cross-sectional dimension of about 40 mm during operation of the device in the subject to avoid passage of any portion of the device through the lower esophageal sphincter or pyloric sphincter of the subject after expansion;
a maximum, cross-sectional dimension of the predetermined shape of about 70 mm for a positioning of the predetermined shape in the pyloric antrum of the subject;
the minimum and maximum cross-sectional dimensions limiting the intragastric device to a minimum volume of $\pi(40\text{ mm})^3/6$ or about 33 ml and a maximum volume of $\pi(70\text{ mm})^3/6$ or about 180 ml; and, a filling material comprising a biocompatible fluid component and a hydrogel component, wherein the filling material has a specific gravity greater than 1.2 and contributes to an in vivo specific gravity of the device that ranges from about 1.2 to about 2.1, the specific gravity functioning to direct the device to the pyloric antrum of the subject to induce gastric discomfort during use of the device;

wherein, the specific gravity of the device allows the device to move freely about the distal stomach and apply pressure to the antrum without otherwise affecting normal gastric function of the subject.

53. The device of claim 52, wherein the device has an in vivo specific gravity ranging from about 1.3 to about 1.6.

54. The device of claim 52, wherein the device has an in vivo specific gravity ranging from about 1.2 to about 1.3.

55. The device of claim 52, wherein the biocompatible fluid is selected from the group consisting of a salt solution, a sugar solution, honey, a sugar alcohol solution, glycerin, or a combination thereof.

56. The device of claim 52, wherein the biocompatible fluid comprises a sugar alcohol solution.

57. The device of claim 52, wherein the casing comprises an ultrasonically visible marker for ultrasonically monitoring the device in vivo.

58. A method of administering the device of claim 52, comprising:
placing the device in a collapsed state in the stomach of the subject; and,
expanding the device after the placing; wherein,
the high specific gravity functions to direct the device to the antrum of the stomach.

59. A method of treating obesity in a subject using the device of claim 52, wherein the method comprises:
placing the device in a collapsed state in the stomach of the subject;
expanding the device; and,
treating the subject for an effective amount of time.

60. The method of claim 59, wherein, the treating includes a deployment period of at least 9 months.

61. A kit comprising the device of claim 52, a filling material having a specific gravity of greater than 1.2, and an insertion catheter designed for administration of the device in the subject.

62. An intragastric device, comprising:
a single flexible and expandable bladder having a predetermined shape upon expansion for contacting the antrum of the stomach of a subject; wherein,
the device is designed to avoid passage of any part of the device beyond the pylorus and lower esophageal sphincter while the bladder is expanded during use in vivo;
the bladder has a high specific gravity material when expanded;
the high specific gravity material contributes to an in vivo specific gravity of the device that ranges from about 1.2 to about 2.1 and functions to direct the device to the pyloric antrum of the subject to induce gastric discomfort during use of the device; and, a filling material comprising a biocompatible fluid component and a hydrogel component, wherein the filling material has a specific gravity greater than 1.2;

wherein,
the intragastric device is limited to a minimum volume of $\pi(40\text{ mm})^3/6$ or about 33 ml and a maximum volume of $\pi(70\text{ mm})^3/6$ or about 180 ml;

the intragastric device is at least substantially leakproof, functioning to provide a volume sufficient to avoid passage of any portion of the device through the lower esophageal sphincter or pyloric sphincter of the subject for a period of at least 9 months; and, the specific gravity of the device allows the device to move freely about the distal stomach and apply pressure to the antrum without otherwise affecting normal gastric function of the subject.

63. The device of claim 62, wherein the device has an in vivo specific gravity ranging from about 1.3 to about 1.6.

64. The device of claim 62, wherein the device has an in vivo specific gravity ranging from about 1.2 to about 1.3.

65. The device of claim 62, wherein the biocompatible fluid is selected from the group consisting of a salt solution, a sugar solution, honey, a sugar alcohol solution, glycerin, or a combination thereof.

66. The device of claim 62, wherein the biocompatible fluid comprises a sugar alcohol solution.

67. The device of claim 62, wherein the casing comprises an ultrasonically visible marker for ultrasonically monitoring the device in vivo.

68. A method of administering the device of claim 62, comprising:
placing the device in a collapsed state in the stomach of the subject; and,
expanding the device after the placing; wherein,
the high specific gravity functions to direct the device to the antrum of the stomach.

69. A method of treating obesity in a subject using the device of claim 62, wherein the method comprises:
placing the device in a collapsed state in the stomach of the subject;
expanding the device; and,
treating the subject for an effective amount of time.

70. The method of claim 69, wherein, the treating includes a deployment period of at least 9 months.

71. A kit comprising the device of claim 62, a filling material having a specific gravity of greater than 1.2, and an insertion catheter designed for administration of the device in the subject.

* * * * *